(12) United States Patent
Sarris et al.

(10) Patent No.: US 7,311,924 B2
(45) Date of Patent: Dec. 25, 2007

(54) COMPOSITIONS AND METHODS FOR TREATING CANCER

(75) Inventors: Andreas H Sarris, Houston, TX (US); Fernando Cabanillas, Houston, TX (US); Patricia M Logan, Vancouver (CA); Clive T R Burge, Brentwood Bay (CA); James H Goldie, Vancouver (CA); Murray S Webb, Delta (CA); Thomas D Madden, Vancouver (CA); Sean C Semple, Vancouver (CA); Quet F Ahkong, Surrey (CA); Sandra K Klimuk, Vancouver (CA)

(73) Assignee: Hana Biosciences, Inc., South San Francisco, CA (US)

( * ) Notice: Subject to any disclaimer, the term of this patent is extended or adjusted under 35 U.S.C. 154(b) by 593 days.

(21) Appl. No.: 10/407,864

(22) Filed: Apr. 3, 2003

(65) Prior Publication Data

US 2004/0071768 A1   Apr. 15, 2004

Related U.S. Application Data

(63) Continuation-in-part of application No. 09/896,812, filed on Jun. 29, 2001, now Pat. No. 7,244,448, and a continuation-in-part of application No. 09/541,436, filed on Mar. 31, 2000, now Pat. No. 6,723,338.

(60) Provisional application No. 60/264,616, filed on Jan. 26, 2001, provisional application No. 60/215,556, filed on Jun. 30, 2000, provisional application No. 60/137,194, filed on Jun. 2, 1999, provisional application No. 60/127,444, filed on Apr. 1, 1999.

(51) Int. Cl.
*A61K 9/127* (2006.01)

(52) U.S. Cl. ...................................................... 424/450

(58) Field of Classification Search ...................... None
See application file for complete search history.

(56) References Cited

U.S. PATENT DOCUMENTS

| | | | |
|---|---|---|---|
| 4,186,183 A | 1/1980 | Steck et al. ................... 424/38 |
| 4,217,344 A | 8/1980 | Vanlerberghe et al. ........ 424/60 |
| 4,235,871 A | 11/1980 | Papahadjopoulos et al. .. 424/19 |
| 4,261,975 A | 4/1981 | Fullerton et al. ............. 424/89 |
| 4,485,054 A | 11/1984 | Mezei et al. ................. 264/4.6 |

(Continued)

FOREIGN PATENT DOCUMENTS

WO          WO 91/17424          11/1991

(Continued)

OTHER PUBLICATIONS

U.S. Appl. No. 08/316,394 entitled "Glycosylated Protein-Liposome Conjugates and Methods for their Preparation," filed Sep. 30, 1994.

(Continued)

*Primary Examiner*—Gollamudi S. Kishore
(74) *Attorney, Agent, or Firm*—Seed Intellectual Property Law Group PLLC

(57) ABSTRACT

This invention provides compositions and methods for treating neoplasias in a mammal. In particular, the invention provides liposome-encapsulated vinca alkaloids, e.g., vinorelbine, and methods of treating a mammal using such compositions.

14 Claims, 19 Drawing Sheets

U.S. PATENT DOCUMENTS

| | | | |
|---|---|---|---|
| 4,501,728 A | 2/1985 | Geho et al. | 424/38 |
| 4,603,044 A | 7/1986 | Geho et al. | 424/9 |
| 4,737,323 A | 4/1988 | Martin et al. | 264/4.3 |
| 4,774,085 A | 9/1988 | Fidler | 424/85.5 |
| 4,837,028 A | 6/1989 | Allen | 424/450 |
| 4,885,172 A | 12/1989 | Bally et al. | 424/450 |
| 4,946,787 A | 8/1990 | Eppstein et al. | 435/240.2 |
| 4,952,408 A | 8/1990 | Rahman | 424/450 |
| 4,957,773 A | 9/1990 | Spencer et al. | 427/39 |
| 5,023,087 A * | 6/1991 | Yau-Young | 424/450 |
| 5,059,421 A | 10/1991 | Loughrey et al. | 424/417 |
| 5,077,056 A | 12/1991 | Bally et al. | 424/450 |
| 5,165,922 A | 11/1992 | Hellstrom et al. | 424/85.8 |
| 5,171,578 A | 12/1992 | Bally et al. | 424/450 |
| 5,534,499 A | 7/1996 | Ansell | 514/25 |
| 5,543,152 A * | 8/1996 | Webb et al. | 424/450 |
| 5,552,156 A | 9/1996 | Burke | 424/450 |
| 5,567,592 A | 10/1996 | Benet et al. | 435/7.21 |
| 5,595,756 A | 1/1997 | Bally et al. | 424/450 |
| 5,714,163 A | 2/1998 | Forssen et al. | 424/450 |
| 5,736,155 A | 4/1998 | Bally et al. | 424/450 |
| 5,741,516 A | 4/1998 | Webb et al. | 424/450 |
| 5,755,788 A * | 5/1998 | Strauss | 623/1.1 |
| 5,785,987 A * | 7/1998 | Hope et al. | 424/450 |
| 5,814,335 A | 9/1998 | Webb et al. | 424/450 |
| 5,820,873 A | 10/1998 | Choi et al. | 424/283.1 |
| 5,837,282 A | 11/1998 | Fenske et al. | 424/450 |
| 5,885,613 A | 3/1999 | Holland et al. | 424/450 |
| 5,976,567 A | 11/1999 | Wheeler et al. | 424/450 |
| 6,056,973 A * | 5/2000 | Allen et al. | 424/450 |
| 6,110,491 A * | 8/2000 | Kirpotin | 424/450 |
| 6,320,017 B1 | 11/2001 | Ansell | 528/310 |
| 6,355,268 B1 | 3/2002 | Slater et al. | 424/450 |
| 6,471,943 B1 * | 10/2002 | Placke et al. | 424/45 |
| 6,566,395 B1 * | 5/2003 | Moran | 514/521 |
| 6,723,338 B1 * | 4/2004 | Sarris et al. | 424/450 |
| 2003/0147945 A1 * | 8/2003 | Tardi et al. | 424/450 |

FOREIGN PATENT DOCUMENTS

| | | |
|---|---|---|
| WO | WO 95/08986 | 4/1995 |
| WO | WO 98/17256 | 4/1998 |
| WO | WO 99/13816 | 3/1999 |
| WO | WO 99/51202 | 10/1999 |
| WO | WO 00/23052 | 4/2000 |

OTHER PUBLICATIONS

U.S. Appl. No. 08/316,407 entitled "Bilayer Stabilizing Components and their use in Forming Programmable Fusogenic Liposomes," filed Sep. 30, 1994.

U.S. Appl. No. 08/996,783 entitled "Polyamide Oligomers," filed Feb. 2, 1998.

Bloomfield, V., "Quasi-Elastic Light Scattering Application in Biochemistry and Biology," *Ann. Rev. Biophys. Bioeng.* 10:421-450, 1981.

Burris, H. et al., "Activity of Topotecan, a New Topoisomerase I Inhibitor, Against Human Tumor Colony-Forming Units in Vitro," *J. Natl. Cancer Inst.* 84(23):1816-1825, Dec. 1992.

Chu, E. et al., *Physician's Cancer Chemotherapy Drug Manual 2002*, Jones and Bartlett Publishers, Sudbury, Massachusetts, 2002.

Clements, M. et al., "Antiangiogenic Potential of Camptothecin and Topotecan," *Cancer Chemother. Pharmacol.* 44:411-416, 1999.

Corbett, T. et al., *Anticancer Drug Development Guide: Preclinical Screening, Clinical Trials, and Approval*, Humana Press Inc., Totowa NJ, 1997, Ch. 5, "In Vivo Methods for Screening and Preclinical Testing" pp. 75-99.

Deamer, D. et al., "Larger Volume Liposomes by an Ether Vaporization Method," *Biochim. et Biophys. Acta* 443:629-634, 1976.

Dumontet, C. et al., "Mechanisms of Action of and Resistance to Antitubulin Agents: Microtubule Dynamics, Drug Transport, and Cell Death," *J. Clin. Oncol.* 17(3):1061-1070, Mar. 1999.

Emerson, D. et al., "In Vivo Antitumor Activity of Two New Seven-Substituted Water-Soluble Camptothecin Analogues," *Cancer Res.* 55:603-609, Feb. 1995.

Erickson-Miller, C. et al., "Differential Toxicity of Camptothecin, Topotecan and 9-Aminocamptothecin to Human, Canine, and Murine Myeloid Progenitors (CFU-GM) in Vitro," *Cancer Chemother. Pharmacol.* 39:467-472, 1997.

Fenske, D. et al., "Ionophore-Mediated Uptake of CiproFloxacin and Vincristine into Large Unilamellar Vesicles Exhibiting Transmembrane Ion Gradients," *Biochim. et Biophys. Acta* 1414:188-204, 1998.

Fraley, R. et al., "Entrapment of a Bacterial Plasmid in Phospholipid Vesicles: Potential for Gene Transfer," *Proc. Natl. Acad. Sci. USA* 76(7):3348-3352, Jul. 1979.

Grochow, L. et al., "Pharmacokinetics and Pharmacodynamics of Topotecan in Patients with Advanced Cancer," *Drug Metabolism and Disposition* 20(5):706-713, 1992.

Gruner, S., *Liposomes—from Biophysics to Therapeutics*, Marcel Dekker, Inc., New York, Ch. 1, "Materials Properties of Liposomal Bilayers," pp. 1-38.

Hardman, W. et al., "Efficacy of Treatment of Colon, Lung and Breast Human Carcinoma Xenografts with: Doxorubicin, Cisplatin, Irinotecan or Topotecan," *Anticancer Research* 19:2269-2274, 1999.

Heath, T., "Covalent Attachment of Proteins to Liposomes," *Methods in Enzymology* 149:111-119, 1987.

Hope, M. et al., "Production of Large Unilamellar Vesicles by a Rapid Extrusion Procedure. Characterization of Size Distribution, Trapped Volume and Ability to Maintaine a Membrane Potential," *Biochim. et Biophys. Acta* 812:55-65, 1985.

Hsiang, Y-H, et al., "Identification of Mammalian DNA Topoisomerase I as an Anticellular Target of the Anticancer Drug Camptothecin," *Cancer Research* 48:1722-1726, Apr. 1988.

Hudson, W. et al., "Xenotransplantation of Human Lymphoid Malignancies is Optimized in Mice with Multiple Immunologic Defects," *Leukemia* 12:2029-2033, 1998.

Kluin-Nelemans, H. et al., "A New Non-Hodgkin's B-Cell Line (DoHH2) with a Chromosomal Translocation t(14;18) (q32;q21)," *Leukemia* 5(3):221-224, Mar. 1991.

King, R.E., *Remington's Pharmaceutical Sciences*, 17$^{th}$ Ed., Mack Publishing Co., Philadelphia, PA, 1985, Part 8, "Pharmaceutical Preparations and Their Manufacture," pp. 1409-1677.

Leonetti, J-P. et al., "Antibody-Targeted Liposomes Containing Oligodeoxyribonucleotides Complementary to Viral RNA Selectively Inhibit Viral Replication," *Proc. Natl. Acad. Sci. USA* 87:2448-2451, Apr. 1990.

Madden, T. et al., "The Accumulation of Drugs within Large Unilamellar Vesicles Exhibiting a Proton Gradient: A Survey," *Chem. and Phys. of Lipids* 53:37-46, 1990.

Mayer, L. et al., "Characterization of Liposomal Systems Containing Doxorubicin Entrapped in Response to pH Gradients," *Biochim. et Biophys. Acta* 1025:143-151, 1990.

Mayer, L. et al., "Techniques for Encapsulating Bioactive Agents into Liposomes," *Chem. and Phys. of Lipids* 40:333-345, 1986.

Mayer, L. et al., "Vesicles of Variable Sizes Produced by a Rapid Extrusion Procedure," *Biochim. et Biophys. Acta* 858:161-168, 1986.

McCabe, F. et al., "Comparative Activity of Oral and Parenteral Topotecan in Murine Tumor Models: Efficacy of Oral Topotecan," *Cancer Investigation* 12(3):308-313, 1994.

Merck Index, 11$^{th}$ ed. 1989, Entry Nos. 9887, 9891, & 9893.

O'Leary, J. et al., "Antiangiogenic Effect of Camptothecin Analogues 9-Amino-20(S)-Campthothecin, Topotecan, and CPT-11 Studied in the Mouse Cornea Model," *Clinical Cancer Research* 5:181-187, Jan. 1999.

Ormrod, D. et al., "TOPOTECAN—A Review if its Efficacy in Small Cell Lung Cancer," *Drugs* 58(3):533-551, Sep. 1999.

Plowman, J. et al., *Anticancer Drug Development Guide: Preclinical Screening, Clinical Trials, and Approval*, Humana Press Inc., Totowa NJ, 1997, Ch. 6, "Human Tumor Xenograft Models in NCI Drug Development," pp. 101-125.

Renneisen, K. et al., "Inhibition of Expression of Human Immunodeficiency Virus-1 in Vitro by Antibody-Targeted Liposomes Containing Antisense RNA to the *env* Region," *J. Biol. Chem.* 265(27):16337-16342, Sep. 1990.

Szoka F., "Comparative Properties and Methods of Preparation of Lipid Vesicles (Liposomes)," *Ann. Rev. Biophys. Bioeng.* 9:467-508. 1980.

Thompson, J. et al., "Animal Models for Studying the Action of Topoisomerase I Targeted Drugs," *Biochim. et Biophys. Acta* 1400:301-319, 1998.

Wall, M. et al., "Plan Tumor Agents. I. The Isolation and Structure of Camptothecin, a Novel Alkaloidal Leukemia and Tumor Inhibitor form *Camptotheca acuminata*," *J. Am. Chem. Soc.* 88:3888-3890, 1966.

Waud, R., *Anticancer Drug Development Guide: Preclinical Screening, Clinical Trials, and Approval*, Humana Press Inc., Totowa NJ, 1997, Ch. 4, "Murine L1210 and P388 Leukemias," pp. 59-74.

Williams, K. et al., "Low Density Lipoprotein Receptor-Independent Hepatic Uptake of a Synthetic, Cholesterol-Scavenging Lipoprotein: Implications for the Treatment of Receptor-Deficient Atherosclerosis," *Proc. Natl. Acad. Sci. USA* 85:242-246, Jan. 1988.

Wozniak, A. et al., "Randomized Trial Comparing Cisplatin Plus Vinorelbine in the Treatment of Advanced Non-Small Cell Lung Cancer: A Southwest Oncology Group Study," *J. Clin. Oncol.* 16(7):2459-2465, Jul. 1998.

* cited by examiner

|  | INDOLENT | TRANSFORMED | RELAPSED LYMPHOMA | REFRACTORY AGGRESSIVE | AGGRESSIVE POST-BMT |
|---|---|---|---|---|---|
| EVALUABLE | 18 | 16 | 37 | 11 | 10 |
| CP/PR | 1 | 5 | 18 | 0 | 2 |
| % RESPONSE | 6 | 31 | 49 | 0 | 20 |
| 95% CONFIDENCE INTERVAL | 0-28 | 11-59 | 32-66 | 0-28 | 1-32 |

Fig. 1

|  | 1 Rx | > 2 Rx | > 2, RESPOND TO LAST Rx | > 2, FAIL LAST Rx |
|---|---|---|---|---|
| EVALUABLE | 11 | 26 | 8 | 18 |
| CR | 4 | — | — | — |
| PR | 4 | 10 | 3 | 7 |
| % RESPONSE | 73 | 38 | 38 | 39 |
| 95% CONFIDENCE INTERVAL | 39-95 | 20-59 | 9-76 | 17-64 |

Fig. 2

CRYO-TEM OF LIPOSOMAL VINBLASTINE AND VINORELBINE

COMPOSITIONS AND METHODS FOR TREATING CANCER

CROSS-REFERENCE TO RELATED APPLICATIONS

This patent application claims priority to U.S. patent application Ser. No. 09/541,436, filed Mar. 31, 2000, now U.S. Pat. No. 6,723,338 and Ser. No. 09/896,812, filed Jun. 29, 2001, now U.S. Pat. No. 7,244,448 and U.S. Provisional Patent Application Nos. 60/127,444, filed Apr. 1, 1999, 60/137,194, filed Jun. 2, 1999, 60/215,556, filed Jun. 30, 2000, and 60/264,616, filed Jan. 26, 2001, each of which is incorporated by reference in its entirety.

BACKGROUND OF THE INVENTION

1. Field of the Invention

This invention relates to compositions and methods, including liposomal vinca alkaloids, for the treatment of neoplasias.

2. Description of the Related Art

Despite years of research into the development of new methods of treatment, many types of cancer, including, e.g., lung cancer and cancers of the lymphatic system, or lymphomas, remain quite common. Lung cancer remains the most common cancer in western countries, and approximately 80% of lung carcinomas are of the non-small cell subtype (NSCLC). Similarly, more than 60,000 people in the United States are diagnosed with lymphoma each year, including more than 55,000 cases of non-Hodgkin's Lymphoma (NHL), and these numbers are constantly increasing. The prognosis for those affected by these diseases is often poor, as the survival rates associated with many cancers, including NSCLC and lymphoma remaining low. Clearly, new methods for treating these diseases are needed.

While traditional treatments for cancers typically depend on the type and stage of the cancer as well as the medical history of the patient, treatment for many cancers includes chemotherapy. Such chemotherapy will often entail the administration of a "cocktail" of compounds, e.g., the formulation CHOP, which includes cyclophosphamide, doxorubicin, vincristine, and prednisone. In addition, chemotherapy may be combined with other forms of cancer therapy, such as radiation therapy.

Alkaloids isolated from the periwinkle plant (Vinca rosea) and derivatives thereof, collectively referred to as "vinca alkaloids," have proven effective for first line treatments of many types of lymphomas, leukemia, and other cancers. Vincristine and vinblastine consist of a catharanthine moiety linked to vindoline, and the structures differ by a single substitution in the vindoline group. Vindesine, a desacetyl carboxyamid derivative of vinblastine, was synthesized later. Subsequently, novel synthetic approaches were used to generate compounds that differed from the natural compounds by the presence of an eight rather than a nine-member catharanthine ring, including vinorelbine tartrate (vinorelbine).

The vinca alkaloids are highly cytotoxic drugs that disrupt microtubules, inhibit cell division and induce apoptosis. Without wishing to be bound to a particular theory, it is believed that the vinca alkaloids exert their cytotoxic effects by binding to tubulin, the protein subunit of microtubules. The formation of vinca alkaloid-tubulin complexes interferes with tubulin polymerization, inhibits microtubule assembly and disrupts the mitotic spindle during cell division, resulting in cellular arrest at metaphase. Vinca alkaloids, including vinorelbine, may also exert cytotoxic effects by interfering with (1) nucleic acid and lipid biosynthesis, (2) cellular respiration, (3) calmodulin-dependent $Ca^{2+}$-transport ATPase activity, and (4) amino acid, cyclic AMP and glutathione metabolism.

Vincristine, vinblastine and vinorelbine are the best-known members of this drug family and are widely used clinically. Despite having similar structures and mechanisms of action, the vinca alkaloids differ in their antitumor activity and toxicities. For example, vincristine is used mostly to treat hematological cancers, is rarely used as a single agent, and neurotoxicity is dose limiting. Vincristine is included in the common chemotherapeutic formulation CHOP. Vincristine, which depolymerizes microtubules and thereby inhibits cell proliferation, is administered in its free form in CHOP. In contrast, vinorelbine is approved for use as a single agent to treat breast and non-small cell lung cancers, and myelosuppression is dose limiting.

Lipid-encapsulated drug formulations may provide advantages over traditional drug-delivery methods. For example, some lipid-based formulations provide longer half-lives in vivo, superior tissue targeting, and decreased toxicity. In efforts to develop more effective cancer treatment, many anticancer or antineoplastic drugs have been encapsulated in liposomes. These include alkylating agents, nitrosoureas, cisplatin, antimetabolites, and anthracyclines. Studies with liposomes containing anthracycline antibiotics have clearly shown reduction of cardiotoxicity and dermal toxicity and prolonged survival of tumor bearing animals compared to controls receiving free drug.

Liposomal anticancer drugs modify drug pharmacokinetics as compared to their free drug counterpart. For a liposomal drug formulation, drug pharmacokinetics are largely determined by the rate at which the carrier is cleared from the blood and the rate at which the drug is released from the carrier. Considerable efforts have been made to identify liposomal carrier compositions that show slow clearance from the blood and long-circulating carriers have been described in numerous scientific publications and patents. Efforts have also been made to control drug leakage rates from liposomal carriers, using for example, transmembrane potential to control release.

Although numerous methods have been described for the formulation of lipid-based drug delivery vehicles (see, e.g., U.S. Pat. No. 5,741,516), previous studies have not demonstrated that liposome-encapsulated vinca alkaloid formulations offer advantages over previous treatments or have efficacy in the in vivo treatment of cancer in a patient. Liposome-encapsulated vincristine has been reported, but successful clinical applications of this technology have never been achieved (see, e.g., U.S. Pat. No. 5,741,516, or U.S. Pat. No. 5,714,163). Indeed, major theoretical and practical uncertainties remain, including uncertainties regarding biodistribution, toxicity, and efficacy. Accordingly, there is a need in the art for liposomal formulations of vinca alkaloids for the treatment of cancer.

BRIEF SUMMARY OF THE INVENTION

It has now been discovered that liposome-encapsulated vinca alkaloids, such as vincristine and vinorelbine, are especially efficacious in first line treatment of neoplasia, as well as for the treatment of relapsed forms of neoplasias, including, e.g., lymphomas such as non-Hodgkin's Lymphomas. Provided herein, therefore, are compositions and methods for the treatment of these and other cancers.

In one embodiment, the invention provides a liposomal composition comprising free and precipitated vinca alkaloid within a liposome. In particular embodiments, the liposome comprises sphingomyelin and cholesterol, and in specific embodiments, the ratio of sphingomyelin to cholesterol is between 75/25 and 50/50 (mol % sphingomyelin/mol % cholesterol) or approximately 55:45 (mol % sphingomyelin/ mol % cholesterol). In additional embodiments, the vinca alkaloid is vincristine, vinblastine, vinorelbine, or vindesine.

In certain embodiments of liposomal compositions comprising free and precipitated vinorelbine within a liposome, the precipitated vinorelbine is at least 10% of the total vinorelbine. In particular embodiments, the ratio of vinorelbine to lipid is 0.01-0.5:1 (w/w), at least 0.1:1 (w/w), or 0.1-0.3:1 (w/w). In one embodiment, the concentration of free vinorelbine within the liposome is less than 20 mM.

In related embodiments, the circulation half-life of encapsulated vinorelbine in blood is at least 0.8 hours, or the half-life of release of vinorelbine from the liposomes in blood is at least 2.0 hours.

In another embodiment, the invention provides a liposomal composition comprising vinorelbine within a lipomsome comprising sphingomyelin and cholesterol. In specific embodiments, the ratio of sphingomyelin to cholesterol is between 75/25 and 50/50 (mol % sphingomyelin/mol % cholesterol), approximately 55:45 (mol % sphingomyelin/ mol % cholesterol), or 0.01-0.5:1 (w/w). In aditional embodiments, the ratio of vinorelbine to lipid is at least 0.1:1 (w/w) or between 0.1-0.3:1 (w/w).

In various embodiments of the liposomal compositions of the invention, the liposomes are between 0.5 and 2.0 microns or between 0.8 and 1.2 microns.

In a related embodiment, the invention includes a method of treating a cancer in a mammal, comprising administering a liposomal composition of the invention to the mammal. In specific embodiments, the cancer is selected from the group consisting of: breast cancer, non-small cell lung cancer, ovarian cancer, prostate cancer, colon cancer, and renal cancer, although the compositions may be used to treat any cancer or tumor. In particular embodiments, the liposomal composition is administered to the mammal in combination with empty liposomes.

In another related embodiment, the invention provides a method of manufacturing a liposomal composition for the treatment of a neoplasia, comprising introducing a vinca alkaloid into a liposome via ionophore-mediated loading. The ionophore may be A23187. In one embodiment, the vinca alkaloid is vinorelbine. The invention further provides liposomal compositions manufactured by a method of the invention.

In a further embodiment, the invention provides a kit for use in the treatment of a neoplasia in a mammal, said kit comprising components useful in the preparation of a liposome-encapsulated vinorelbine, instructions for preparing the liposome-encapsulated vinorelbine, and instructions for the use of the liposome-encapsulated vinorelbine in the treatment of the neoplasia.

In a related embodiment, the invention includes a kit for use in the treatment of a neoplasia in a mammal, said kit comprising a stable formulation of liposome-encapsulated vinorelbine and instructions for the use of the liposome-encapsulated vinorelbine in the treatment of the neoplasia.

In one aspect, this invention provides a method for treating a relapsed cancer in a mammal, the method comprising administering to the mammal a pharmaceutical composition comprising a liposome-encapsulated vinca alkaloid. In one embodiment, the relapsed cancer is a non-Hodgkin's Lymphoma.

In another aspect, the present invention provides a method of treating a non-Hodgkin's Lymphoma in a patient, the method comprising administering to the patient a pharmaceutical composition comprising a liposome-encapsulated vinca alkaloid, wherein the composition is free of cardiolipin.

In one embodiment, the non-Hodgkin's Lymphoma is a member selected from the group consisting of aggressive NHL, transformed NHL, indolent NHL, relapsed NHL, refractory NHL, low grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, diffuse large B-cell lymphoma, and acute lymphoblastic lymphoma.

In one embodiment, the vinca alkaloid is vincristine, vinblastine, vinorelbine, or vindesine. In another embodiment, the liposome comprises distearoylphosphatidylcholine or sphingomyelin. In another embodiment, the liposome further comprises cholesterol. In another embodiment, the liposome comprise a pH gradient. In another embodiment, the pH at the interior of the liposomes is lower than the pH at the exterior.

In another embodiment, the mammal is a human. In another embodiment, the mammal has previously undergone at least one chemotherapy treatment. In another embodiment, the chemotherapy treatment comprised administration of a free-form vinca alkaloid, such as vincristine, vinblastine, vindesine, or vinorelbine. In other embodiments, the chemotherapy treatment included an anthracycline-containing combination therapy. In one such embodiment, the anthracycline was doxorubicin. In another embodiment, the mammal has exhibited a partial or complete response to the chemotherapy prior to a relapse of the cancer. In another embodiment, the relapse is a second relapse.

In another embodiment, the liposome-encapsulated vinca alkaloid is administered systemically by intravenous delivery. In another embodiment, the liposome-encapsulated vincristine is co-administered with cyclophosphamide, doxorubicin, and prednisone, forming CHOP (or, in this case, "lipo-CHOP"). In another embodiment, the liposome-encapsulated vinca alkaloid is co-administered with at least one additional anti-tumor agent. In another embodiment, the additional anti-tumor agent is an anti-tumor monoclonal antibody, such as Oncolym™, Rituxan™, or Bexxar™. In another embodiment, the additional anti-tumor agent is an antisense drugs or an anti-tumor vaccine. In another embodiment, the liposome-encapsulated vinca alkaloid is co-administered with a prophylactic or therapeutic treatment for neurotoxicity, such as Neurontin™ gabapentin (Neurotonin).

In another embodiment, the liposome-encapsulated vinca alkaloid is administered to the mammal once every 7-21 days, preferably every 14 days. In another embodiment, the liposome encapsulated vinca alkaloid is administered at a dosage falling within a range of about 1.4 to about 2.4 mg/m$^2$.

The present invention provides an improvement on conventional methods of treating cancer. In particular, the present invention provides a method for treating an aggressive, relapsed, transformed, indolent, or refractory lymphoma in a mammal, the improvement comprising administering a liposome-encapsulated vinca alkaloid such as vincristine (or other liposome-encapsulated therapeutic agent) to the mammal. In addition, the present invention provides a basis for an improved combination chemotherapy for use in first-line treatment of non-Hodgkin's Lymphoma.

Kits including the herein-described formulations, and for preparing the herein-described formulations, as well as instructions for their use are also included.

The present invention also provides the use of a liposome-encapsulated vinca alkaloid in the preparation of a medicament for the treatment of a neoplasia, including, e.g., non-Hodgkin's Lymphoma. In certain uses, the neoplasia is a relapsed, indolent, aggressive, or transformed neoplasia, e.g., non-Hodgkin's Lymphoma. In other uses, the medicament is used as a first line treatment for a neoplasia. In preferred uses, the vinca alkaloid is vincristine. In other preferred uses, the vinca alkaloid is present in the medicament at a dosage, e.g., of about 2.4 to about 3.4 mg/m$^2$, and is administered once every 7-21 days, most preferably every 14 days.

Definitions

"Neoplasia," as used herein, refers to any aberrant growth of cells, tumors, malignant effusions, warts, polyps, nonsolid tumors, cysts and other growths. A site of neoplasia can contain a variety of cell types, including but not limited, to neoplastic cells, vascular endothelia, or immune system cells, such as macrophages and leukocytes, etc.

A "cancer" in a mammal refers to any of a number of conditions caused by the abnormal, uncontrolled growth of cells. Cells capable of causing cancer, called "cancer cells", possess a number of characteristic properties such as uncontrolled proliferation, immortality, metastatic potential, rapid growth and proliferation rate, and certain typical morphological features. Often, cancer cells will be in the form of a tumor, but such cells may also exist alone within a mammal, or may be a non-tumorigenic cancer cell, such as a leukemia cell. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer (e.g., CA125, PAP, PSA, CEA, AFP, HCG, CA 19-9, CA 15-3, CA 27-29, LDH, NSE, and others), and detecting a genotype indicative of a cancer (e.g., TP53, ATM, etc.). However, a negative result in one or more of the above detection methods does not necessarily indicate the absence of cancer, e.g., a patient who has exhibited a complete response to a cancer treatment may still have a cancer, as evidenced by a subsequent relapse.

"Systemic delivery," as used herein, refers to delivery that leads to a broad bio-distribution of a compound within an organism. Systemic delivery means that a useful, preferably therapeutic, amount of a compound is exposed to most parts of the body. To obtain broad bio-distribution generally requires a route of introduction such that the compound is not rapidly degraded or cleared (such as by first pass organs (liver, lung, etc.) or by rapid, nonspecific cell binding) before reaching a disease site. Systemic delivery of liposome-encapsulated vinca alkaloids is preferably obtained by intravenous delivery.

"Lymphoma" refers to a malignant growth of B or T cells in the lymphatic system. "Lymphoma" includes numerous types of malignant growths, including Hodgkin's Lymphoma and non-Hodgkin's lymphoma (NHL).

"Non-Hodgkin's Lymphoma" refers to a malignant growth of B or T cells in the lymphatic system that is not a Hodgkin's Lymphoma (which is characterized, e.g., by the presence of Reed-Sternberg cells in the cancerous area). Non-Hodgkin's lymphomas encompass over 29 types of lymphoma, the distinctions between which are based on the type of cancer cells. The particular classification depends on the particular system of classification used, such as the Working formulation, the Rappaport classification, and the REAL classification. In preferred embodiments, the REAL classification is used.

A "relapsed cancer" or lymphoma refers to a cancer or lymphoma that has recurred following prior complete or partial remission in response to a prior treatment. Recurrence can be defined in any way, including a reappearance or re-growth of a tumor as detected by clinical, radiological, or biochemical assays, or by an increased level of a cancer marker. Prior treatments can include, but are not limited to, chemotherapy, radiation therapy, and bone marrow transplantation.

An "indolent" non-Hodgkin's Lymphoma is a classification that includes slow growing forms of lymphoma. They encompass what are called low grade and some categories of intermediate grade NHL in the Working Formulation. Indolent NHLs are sometimes not responsive to conventional cancer therapies such as chemotherapy and radiation therapy.

A "transformed" non-Hodgkin's Lymphoma is a classification sometimes employed to describe an indolent NHL which acquires an aggressive aspect and becomes more responsive to standard chemotherapies.

Patients with "refractory cancer" or "refractory lymphoma" are those who have failed to achieve complete remission on their first course of combination chemotherapy, or to patients who have failed to achieve complete or partial remission on subsequent chemotherapy. "Primary refractory" patients are those who have never achieved complete remission even at first treatment.

A "stable disease" is a state wherein a therapy causes cessation of growth or prevalence of a tumor or tumors as measured by the usual clinical, radiological and biochemical means, although there is no regression or decrease in the size or prevalence of the tumor or tumors, i.e., cancer that is not decreasing or increasing in extent or severity.

"Partial response" or "partial remission" refers to the amelioration of a cancerous state, as measured by tumor size and/or cancer marker levels, in response to a treatment. Typically, a "partial response" means that a tumor or tumor-indicating blood marker has decreased in size or level by about 50% in response to a treatment. The treatment can be any treatment directed against cancer, but typically includes chemotherapy, radiation therapy, hormone therapy, surgery, cell or bone marrow transplantation, immunotherapy, and others. The size of a tumor can be detected by clinical or by radiological means. Tumor-indicating markers can be detected by means well known to those of skill, e.g., ELISA or other antibody-based tests.

A "complete response" or "complete remission" means that a cancerous state, as measured by, for example, tumor size and/or cancer marker levels, has disappeared following a treatment such as chemotherapy, radiation therapy, hormone therapy, surgery, cell or bone marrow transplantation, or immunotherapy. The presence of a tumor can be detected by clinical or by radiological means. Tumor-indicating markers can be detected by means well known to those of skill, e.g., ELISA or other antibody-based tests. A "complete response" does not necessarily indicate that the cancer has been cured, however, as a complete response can be followed by a relapse.

"Chemotherapy" refers to the administration of chemical agents that inhibit the growth, proliferation and/or survival of cancer cells. Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapy can include any chemical agent that inhibits, or is designed to inhibit, a cancerous cell or a cell likely to become cancerous. Such agents are often administered, and are often most effective, in combination, e.g., in the formulation CHOP.

"Radiation therapy" refers to the administration of radioactivity to an animal with cancer. Radiation kills or inhibits the growth of dividing cells, such as cancer cells.

"Surgery" is the direct removal or ablation of cells, e.g., cancer cells, from an animal. Most often, the cancer cells will be in the form of a tumor (e.g., resulting from a lymphoma), which is removed from the animal.

"Hormone therapy" refers to the administration of compounds that counteract or inhibit hormones, such as estrogen or androgen, that have a mitogenic effect on cells. Often, these hormones act to increase the cancerous properties of cancer cells in vivo.

"Immunotherapy" refers to methods of enhancing the ability of an animal's immune system to destroy cancer cells within the animal.

A "free-form" therapeutic agent, or "free" therapeutic agent, refers to a therapeutic agent that is not liposome-encapsulated. Usually, a drug is presumed to be "free, or in a "free-form," unless specified otherwise. A vinca alkaloid in free form may still be present in combination with other reagents, however, such as other chemotherapeutic compounds, a pharmaceutical carrier, or complexing agents, i.e. as used herein the term only specifically excludes lipid formulations of the vinca alkaloids.

BRIEF DESCRIPTION OF THE DRAWINGS

FIG. 1 provides results for a clinical trial using the herein-described methods, in particular regarding the efficacy of the methods in the treatment of indolent, transformed, relapsed, and aggressive post bone-marrow transplant (BMT) forms of non-Hodgkin's Lymphoma.

FIG. 2 provides results concerning the response to liposomal vincristine in Relapsed Aggressive NHL, particularly with regard to the effect of the prior regimen number.

DETAILED DESCRIPTION OF THE INVENTION

Figure 3:
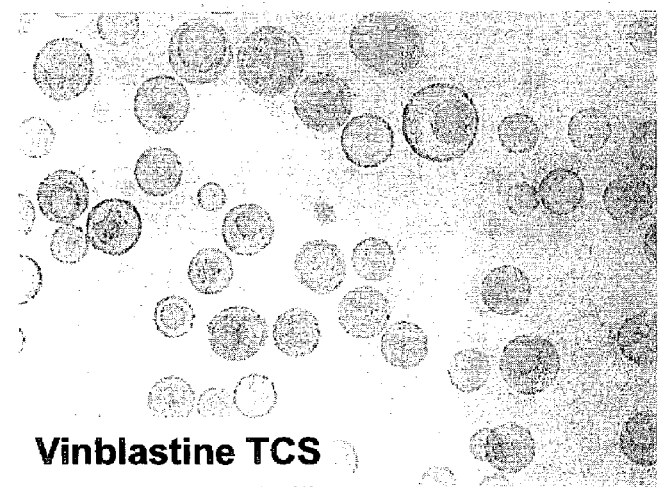
FIG. 3 provides cryo-TEM micrographs of liposomal vinorelbine and liposomal vinblastine (D/L ratio 0.26 w/w) that show the encapsulated vinca alkaloids as amorphous precipitates inside some of the vesicles.
Figure 3:
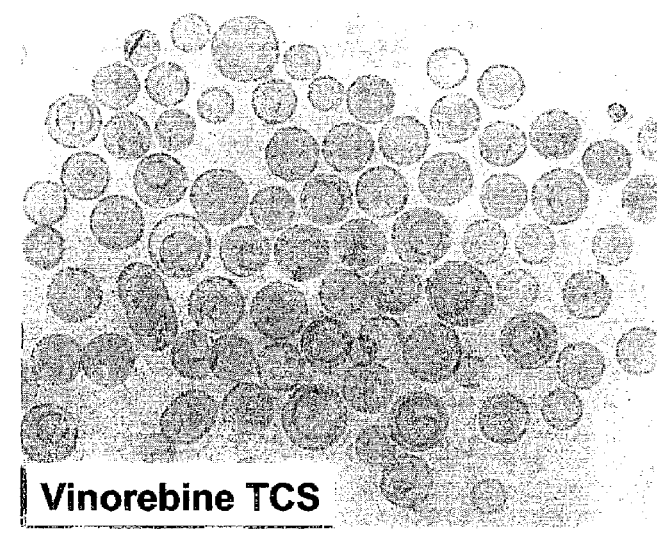

This invention provides compositions and methods for treating neoplasia in a patient. This invention is based on the discovery that liposome-encapsulated vinca alkaloids are unusually effective in the treatment of a variety of forms of cancer, including lymphoma. In particular, the surprising discovery was made that the administration of liposome-encapsulated vinca alkaloids increases the median survival of patients with lymphoma. In one embodiment, vincristine, encapsulated in a sphingomyelin and cholesterol based liposome, is used in the treatment of non-Hodgkin's Lymphoma, especially relapsed forms of non-Hodgkin's Lymphoma (NHL). Accordingly, the invention also provides, inter alia, methods of treating indolent, transformed, and aggressive forms of NHL.

The present invention further demonstrates that vinorelbine, encapsulated in a sphingomyelin and cholesterol based liposome, is useful in the treatment of a variety of cancers. Accordingly, the invention provides liposomal formulations of vinorelbine and methods of using the same in the treatment of a variety of cancers, including, but not limited to, breast cancer, prostate cancer, colon cancer, renal cancer, and non-small cell lung cancer.

The lipsomal vinca alkaloids of the invention may be administered as first line treatments or as secondary treatments. In addition, they may be administered as a primary chemotherapeutic treatment or as adjuvant or neoadjuvant chemotherapy. For example, treatments of relapsed, indolent, transformed, and aggressive forms of non-Hodgkin's Lymphoma may be administered following at least one course of a primary anti-cancer treatment, such as chemotherapy and/or radiation therapy, followed by at least one partial or complete response to the at least one treatment. In any of these embodiments, the liposome-encapsulated vinca alkaloids can be provided as a single agent or in a combination therapy.

The present invention further provides dosages and dose scheduling of liposomal vinca alkaloids, including, e.g., liposomal vinorelbine, liposomal vincristine, and liposomal vinblastine, for treatment of solid and non-solid tumors with reduced toxicity.

I. Cancers Treatable with Lipid-Encapsulated Vinca Alkaloids

The compositions and methods described herein can be used to treat any type of cancer, including, but not limited to, neuroblastomas, myelomas, breast cancers, prostate cancers, colon cancer, renal cancer, lymphomas, and non small cell lung cancer. Patients or subjects treated for cancer using compositions and methods of the invention include, but are not limited to, mammals, including humans, other primates, domestic animals, such as dogs and cats, and livestock, such as cows, pigs, and sheep.

In certain embodiments, lipsomal vinca alkaloids, e.g., liposomal vinorelbine, are used to treat primary cancers and tumors, and in other embodiments, liposomal vinca alkaloids are used to treat cancers and tumors previously shown to be responsive to free or unencapsulated vinca alkaloids, including, e.g., breast cancer, ovarian cancer, and non-small cell lung cancer. The compositions and methods can be applied to both solid and non-solid tumors, including cancers of the blood and lymphatic systems, such as lymphomas, leukemia, and myelomas.

In certain embodiments, the present methods are used to treat any of the large number of lymphomas. For example, both Hodgkin's and non-Hodgkin's lymphomas can be treated using the methods described herein. In particularly preferred embodiments, the methods are used to treat non-Hodgkin's Lymphoma (NHL), including any type of NHL as defined according to any of the various classification systems such as the Working formulation, the Rappaport classification and, preferably, the REAL classification. Such lymphomas include, but are not limited to, low-grade, intermediate-grade, and high-grade lymphomas, as well as both B-cell and T-cell lymphomas. Included in these categories are the various types of small cell, large cell, cleaved cell, lymphocytic, follicular, diffuse, Burkitt's, Mantle cell, NK cell, CNS, AIDS-related, lymphoblastic, adult lymphoblastic, indolent, aggressive, transformed and other types of lymphomas. The methods of the present invention can be used for adult or childhood forms of lymphoma, as well as lymphomas at any stage, e.g., stage I, II, III, or IV. The various types of lymphomas are well known to those of skill, and are described, e.g., by the American Cancer Society (see, e.g., www3.cancer.org).

The methods described may also be applied to any form of leukemia, including adult and childhood forms of the disease. For example, any acute, chronic, myelogenous, and lymphocytic form of the disease can be treated using the methods of the present invention. In preferred embodiments, the methods are used to treat Acute Lymphocytic Leukemia (ALL). More information about the various types of leukemia can be found, inter alia, from the Leukemia Society of America (see, e.g., www.leukemia.org).

II. First-Line Treatments

In numerous embodiments of the present invention, liposome-encapsulated vinca alkaloids will be used as a first-line treatment for cancer. As used herein, "first-line treatment" refers to a primary treatment for a patient presenting with a cancer, in contrast to a relapsed or refractory cancer.

When used as a single agent in first-line treatment, dosages and dose scheduling is preferably the same as single agent treatment for relapsed cancer. When used in combination regimes, as described infra, dosages and dose scheduling may be revised to correspond to the preferred regimen for the combination.

III. Relapsed or Refractory Forms of the Diseases

The present methods can be used to treat primary, relapsed, transformed, or refractory forms of cancer. Often, patients with relapsed cancers have undergone one or more treatments including chemotherapy, radiation therapy, bone marrow transplants, hormone therapy, surgery, and the like. Of the patients who respond to such treatments, they may exhibit stable disease, a partial response (i.e., the tumor or a cancer marker level diminishes by at least 50%), or a complete response (i.e., the tumor as well as markers become undetectable).

In many cases, patients respond initially to such first-line treatments, but subsequently suffer a relapse, i.e., a tumor reappears or resumes growing. Following one such relapse, patients are often treated with further chemotherapy, e.g., with CHOP or with other formulations, or, in some cases, the patients are treated with other procedures such as bone marrow transplantation. Again, in many cases, patients initially respond to such additional treatments, but subsequently suffer another relapse. In general, the more relapses a patient suffers, the less agreement there is in the art concerning optimal subsequent treatment. In other cases, a patient fails to respond at all to a treatment, even initially, and is thus said to have a refractory cancer. In such cases as well, little agreement exists in the art regarding optimal subsequent treatment.

In certain embodiments, the methods provided herein will be used to treat a patient that has undergone a single course of treatment for a cancer, has partially or completely responded to such treatment, and has subsequently suffered a relapse. In other embodiments, patients are treated who have undergone more than one course of treatment, have responded more than once, and have subsequently suffered more than one relapse. The previous course of treatment can include any anti-cancer treatment, including chemotherapy, radiation therapy, bone marrow transplant, etc. The previous course of treatment may have included treatment with the free form of the drug being used according to the invention in a liposomal formuation, for example.

In certain embodiments of the present invention, liposomal alkaloids are employed against "resistant" cancers, i.e., cancers which have previously exhibited a complete response to a treatment, but which subsequently manifest a resistance to second or later course of treatment.

IV. Vinca and Other Alkaloids

The present invention can include the use of any naturally occurring alkaloid, including vinca alkaloids, or any synthetic derivative of a naturally occurring alkaloid. Vinca alkaloids include, but are not limited to, vinblastine, vincristine, vindoline, vindesine, vinleurosine, vinrosidine, vinorelbine, or derivatives thereof (see, e.g., the Merck Index, $11^{th}$ Edition (1989) entries 9887, 9891, and 9893, for vinblastine, vincristine, and vindoline). Examples of other suitable alkaloids include, but are not limited to, the podophyllins, podophyllotoxins, and derivatives thereof (e.g., etoposide, etoposide phosphate, teniposide, etc.), the camptothecins (e.g., irinotecan, topotecan, etc.) the taxanes (taxol, etc.), and derivatives thereof. All of the above compounds are well known to those of skill and are readily available from commercial sources, by synthesis, or by purification from natural sources. All such alkaloids are included within the term "active agent," as used herein.

In certain embodiments, the vinca alkaloid used in the present invention is vincristine. Vincristine, also known as leurocristine sulfate, 22-oxovincaleukoblastine, Kyocristine, vincosid, vincrex, oncovin, Vincasar PFS®, or VCR, is commercially available from any of a number of sources, e.g., Pharmacia & Upjohn, Lilly, IGT, etc. It is often supplied as vincristine sulfate, e.g., as a 1 mg/mL solution.

In other preferred embodiments, the vinca alkaloid used in the present invention is vinorelbine. Vinorelbine includes vinorelbine tartrate. Vinorelbine (5'-noranhydrovinblastine) is a semisynthetic vinca alkaloid structurally distinguished from other members of its class by the modification of the catharanthine nucleus rather than the vindoline ring. Vinorelbine has shown efficacy in NSCLC treatment, alone or in combination with other drugs. Vinorelbine tartrate (Navelbine®) is commercially available from Glaxo Wellcome Inc. (Research Triangle Park, N.C.).

In other preferred embodiments, the vinca alkaloid is vinblastine. Vinblastine is mainly useful for treating Hodgkin's disease, lymphocytic lymphoma, histiocytic lymphoma, advanced testicular cancer, advanced breast cancer, Kaposi's sarcoma, and Letterer-Siwe disease. Vinblastine is given intravenously to treat Kaposi's sarcoma, often in combination with other drugs. Vinblastine (Velban®, Velsar®) is commercially available from Eli Lilly (Indianapolis, Ind.).

The present invention can comprise the use of a single vinca alkaloid or multiple, co-administered vinca alkaloids. In addition, the one or more vinca alkaloids can be combined with other compounds or molecules, such as other antineoplastic agents. In certain embodiments, such combinations of vinca alkaloids and/or other compounds can be made prior to liposomal formulation, thereby creating a combination within a single liposome. In other embodiments, liposome-encapsulated vinca alkaloids are formulated and subsequently combined with the other molecules, which can themselves be free-form or liposome-encapsulated.

Any of the therapeutic agents described herein, including liposome-encapsulated alkaloids, can be subjected to pre-clinical testing in well known models of human diseases. In vivo models of human lymphoma include mice carrying the non-Hodgkin's B-cell line DoHH2 (Kluin-Nelemans H C, et al. (1991) *Leukemia* 5(3) 221-224), or mice carrying Daudi or Raji cell xenografts (see, for example Hudson, Wash. et al. (1998) *Leukemia* 12(12): 2029-2033). Many other oncological models can also be used and are known to those skilled in the art.

V. Lipids

Any of a number of lipids can be used to prepare the liposomes of the present invention, including amphipathic, neutral, cationic, and anionic lipids. Such lipids can be used alone or in combination, and can also include bilayer stabilizing components such as polyamide oligomers (see, e.g., U.S. Pat. No. 6,320,017, "Polyamide Oligomers", by Ansell), peptides, proteins, detergents, lipid-derivatives, such as PEG coupled to phosphatidylethanolamine and PEG conjugated to ceramides (see, U.S. Pat. No. 5,885,613). In a preferred embodiment, cloaking agents, which reduce elimination of liposomes by the host immune system, can also be included, such as polyamide-oligomer conjugates, e.g., ATTA-lipids, (see, U.S. patent application Ser. No. 08/996,783, filed Feb. 2, 1998) and PEG-lipid conjugates (see, U.S. Pat. Nos. 5,820,873, 5,534,499 and 5,885,613).

Any of a number of neutral lipids can be included, referring to any of a number of lipid species which exist either in an uncharged or neutral zwitterionic form at physiological pH, including diacylphosphatidylcholine, diacylphosphatidylethanolamine, ceramide, sphingomyelin, cephalin, cholesterol, cerebrosides, and diacylglycerols.

In preferred embodiments, the lipid used is sphingomyelin. In particularly preferred embodiments, the lipid comprises sphingomyelin and cholesterol. In such embodiments, the ratio of sphingomyelin to cholesterol is typically between about 75/25 (mol % sphingomyelin/mol % cholesterol) and about 50/50 (mol % sphingomyelin/mol % cholesterol), preferably between about 70/30 and 55/45 (mol % sphingomyelin/mol % cholesterol), and most preferably about 55/45 (mol % sphingomyelin/mol % cholesterol). Such ratios, may be altered, however, by the addition of other lipids into the present formulations.

Cationic lipids, which carry a net positive charge at physiological pH, can readily be incorporated into liposomes for use in the present invention. Such lipids include, but are not limited to, N,N-dioleyl-N,N-dimethylammonium chloride ("DODAC"); N-(2,3-dioleyloxy) propyl-N,N-N-triethylammonium chloride ("DOTMA"); N,N-distearyl-N,N-dimethylammonium bromide ("DDAB"); N-(2,3-dioleyloxy)propyl)-N,N,N-trimethylammonium chloride ("DOTAP"); 3β-(N-(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as LIPOFECTIN (including DOTMA and DOPE, available from GIBCO/BRL), LIPOFECTAMINE (comprising DOSPA and DOPE, available from GIBCO/BRL), and TRANSFECTAM (comprising DOGS, in ethanol, from Promega Corp.).

Anionic lipids suitable for use in the present invention include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

In numerous embodiments, amphipathic lipids will be used. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

The liposomes used in the present invention can be multilamellar or unilamellar, which can be formed using the methods disclosed herein and other methods known to those of skill in the art.

Also suitable for inclusion in the present invention are programmable fusion lipid formulations. Such formulations have little tendency to fuse with cell membranes and deliver their payload until a given signal event occurs. This allows the lipid formulation to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the liposome membrane over time. By the time the formulation is suitably distributed in the body, it has lost sufficient cloaking agent so as to be fusogenic. With other signal events, its is desirable to choose a signal that is associated with the disease site or target cell, such as increased temperature at a site of inflammation.

VI. Preparation of Liposomes

A variety of methods are available for preparing liposomes as described in, e.g., Szoka, et al., *Ann. Rev. Biophys. Bioeng.*, 9:467 (1980), U.S. Pat. Nos. 4,186,183, 4,217,344, 4,235,871, 4,261,975, 4,485,054, 4,501,728, 4,774,085, 4,837,028, 4,946,787, PCT Publication No. WO 91/17424, Deamer and Bangham, *Biochim. Biophys. Acta*, 443:629-634 (1976); Fraley, et al., *Proc. Natl. Acad. Sci. USA*, 76:3348-3352 (1979); Hope, et al., *Biochim. Biophys. Acta*, 812:55-65 (1985); Mayer, et al., *Biochim. Biophys. Acta*, 858:161-168 (1986); Williams, et al., *Proc. Natl. Acad. Sci.*, 85:242-246 (1988), the text *Liposomes*, Marc J. Ostro, ed., Marcel Dekker, Inc., New York, 1983, Chapter 1, and Hope, et al., *Chem. Phys. Lip.*, 40:89 (1986), all of which are incorporated herein by reference. Suitable methods include, but are not limited to, sonication, extrusion, high pressure/homogenization, microfluidization, detergent dialysis, calcium-induced fusion of small liposome vesicles, and ether-infusion methods, all of which are well known in the art.

Alternative methods of preparing liposomes are also available. For instance, a method involving detergent dialysis based self-assembly of lipid particles is disclosed and claimed in U.S. Pat. No. 5,976,567 issued to Wheeler, et al., which avoids the time-consuming and difficult to-scale drying and reconstitution steps. Further methods of preparing liposomes using continuous flow hydration are under development and can often provide the most effective large scale manufacturing process.

One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents, such as deoxycholate.

Unilamellar vesicles can be prepared by sonication or extrusion. Sonication is generally performed with a tip sonifier, such as a Branson tip sonifier, in an ice bath. Typically, the suspension is subjected to severed sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass. Unilamellar vesicles can also be made by dissolving phospholipids in ethanol and then injecting the lipids into a buffer, causing the lipids to spontaneously form unilamellar vesicles. Also, phospholipids can be solubilized into a detergent, e.g., cholates, Triton X, or n-alkylglucosides. Following the addition of the drug to the solubilized lipid-detergent micelles, the detergent is removed by any of a number of possible methods including dialysis, gel filtration, affinity chromatography, centrifugation, and ultrafiltration.

Following liposome preparation, the liposomes which have not been sized during formation may be sized to achieve a desired size range and relatively narrow distribution of liposome sizes. A size range of about 0.2-0.4 microns allows the liposome suspension to be sterilized by filtration through a conventional filter. The filter sterilization method can be carried out on a high through-put basis if the liposomes have been sized down to about 0.2-0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.*, 10:421-450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve gradual reduction in liposome size. For use in the present invention, liposomes having a size ranging from about 0.05 microns to about 0.40 microns are preferred. In preferred embodiments, liposomes are between about 0.05 and about 0.2 microns, and in other preferred embodiments, liposomes are between 0.08 and 0.12 microns.

In preferred embodiments, empty liposomes are prepared using conventional methods known to those of skill in the art.

In one embodiment, the liposomes used in the present invention will comprise a pH gradient across the membrane. In particularly preferred embodiments, the pH is lower at the interior of the liposomes than at the exterior. Such gradients can be achieved, e.g., by formulating the liposomes in the presence of a buffer with a low pH, e.g., having a pH between about 2 and about 6, and subsequently transferring the liposomes to a higher pH solution. In preferred embodiments, the pH is between about 3 and 5, and in most preferred embodiments, the pH is about 4. Any of a number of buffers can be used, such as citrate. In one embodiment, the liposomes used in the present invention comprise a transmembrane potential, while in another embodiment, liposomes of the invention do not comprise a transmembrane potential.

Subsequently, before or after sizing, the external pH can be raised, e.g., to about 7 or 7.5, by the addition of a suitable buffer, such as a sodium phosphate buffer. Raising the external pH creates a pH gradient across the liposomal membrane, thereby promoting efficient drug loading and retention.

Liposomes prepared according to these methods can be stored for substantial periods of time prior to drug loading and administration to a patient. For example, liposomes can be dehydrated, stored, and subsequently rehydrated, loaded with one or more vinca alkaloids, and administered. Dehydration can be accomplished, e.g., using standard freeze-drying apparatus, i.e., they are dehydrated under low pressure conditions. Also, the liposomes can be frozen, e.g., in liquid nitrogen, prior to dehydration. Sugars can be added to the liposomal environment, e.g., to the buffer containing the liposomes, prior to dehydration, thereby promoting the integrity of the liposome during dehydration. See, e.g., U.S. Pat. No. 5,077,056 or 5,736,155.

In numerous embodiments, the empty liposomes are first formulated in low pH buffer, and then manipulated in one of a variety of ways to obtain liposomes of the desired size. Methods for sizing liposomes include sonication, by bath or by probe, or homogenization. Preferably, following such treatments, the liposomes are between about 0.05 to 0.45 microns. Most preferably, the liposomes are between about 0.05 and about 0.2 microns. In one embodiment, the liposomes are between 0.08 and 0.12 microns. Such sized liposomes can then be sterilized by filtration. Also, particle size distribution can be monitored by conventional laser-beam particle size discrimination or the like. In addition, methods of reducing liposome sizes to a relatively well defined size distribution are known, e.g., one or more cycles of extrusion of the liposomes through a small-pore polycarbonate membrane or an asymmetric ceramic membrane.

The present invention also provides liposomal compositions (e.g., vinorelbine) in kit form. The kit can comprise a ready-made formulation, or a formulation that requires mixing of the medicament before administration. The kit will typically comprise a container that is compartmentalized for holding the various elements of the kit. The kit will contain the liposomal compositions of the present invention or the components thereof, possibly in dehydrated form, with instructions for their rehydration and administration.

VII. Preparation of Liposome-Encapsulated Vinca Alkaloids

Preparation of liposomal formulations having active agents (e.g., vinorelbine, vincristine, etc.) requires loading of the drug into the liposomes. Loading can be either passive or active. Passive loading generally requires addition of the drug to the buffer at the time of the reconstitution step. This allows the drug to be trapped within the liposome interior, where it will remain if it is not lipid soluble, and if the vesicle remains intact (such methods are employed, for example, in PCT Publication No. WO 95/08986, the teachings of which are incorporated herein by reference).

In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. The resulting liposomes encompassing the active agent can then be sized as described above.

Active loading is in many ways preferable, and a wide variety of therapeutic agents can be loaded into liposomes with encapsulation efficiencies approaching 100% by using a transmembrane pH or ion gradient (see, Mayer, et al., Biochim. Biophys. Acta 1025:143-151 (1990) and Madden, et al., Chem. Phys. Lipids 53:37-46 (1990)). Numerous ways of active loading are known to those of skill in the art. All such methods involve the establishment of some form of gradient that draws lipophilic compounds into the interior of liposomes where they can reside for as long as the gradient is maintained. Very high quantities of the desired drug can be obtained in the interior, so much that the drug may precipitate out on the interior and generate a continuing uptake gradient.

Transmembrane potential loading has been described in detail in U.S. Pat. Nos. 4,885,172; 5,059,421; 5,171,578; and 5,837,282 (which teaches ionophore loading), each of which is incorporated herein by reference. Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or protein-liposome complexes and the drug is loaded into the liposome by means of the transmembrane potential. The transmembrane potential is generated by creating a concentration gradient for one or more charged species (e.g., $Na^+$, $K^+$, and/or $H^+$) across the membranes. This concentration gradient is generated by producing liposomes having different internal and external media and has an associated proton gradient. Drug accumulation can then occur in a manner predicted by the Henderson-Hasselbach equation.

Particularly preferred for use with the instant invention in loading vinca alkaloids, e.g., vinorelbine, is ionophore-mediated loading as disclosed and claimed in U.S. Pat. No. 5,837,282, the teachings of which are incorporated by reference herein. One example of an ionophore used in this procedure is A23187. The ionophore-mediated loading is an electroneutral process and does not result in formation of a transmembrane potential. With hydrogen ion transport into the vesicle there is concomitant magnesium ion transport out of the vesicle in a 2:1 ratio (i.e. no net charge transfer). In the case of topotecan, it is thought that the agent crosses the membrane in a neutral state (no charge). Upon entry into the vesicle, topotecan becomes positively charged. As ionophore-mediated loading is an electroneutral process, there is no transmembrane potential generated.

In one particular embodiment, compositions of vinorelbine-loaded liposomes are contained in a phosphate-buffered sucrose solution, such as 300 mM sucrose, 10 mM phosphate at pH 7.0. In certain embodiments, liposomes comprising vinorelbine do not comprise an internal buffer solution, and the intravesicular solution may be 450 mM magnesium sulfate, for example.

Preferred methods of preparing liposome-encapsulated vinca alkaloids for use in the present invention are discussed, e.g., in U.S. Pat. Nos. 5,741,516, 5,814,335 and 5,543,152, each of which is assigned to Inex Pharmaceuticals Corp. and is incorporated herein by reference. In a preferred embodiment, liposomal vinca alkaloids are prepared prior to use from a kit including 3 or more vials. At least one of the vials contains a vinca alkaloid solution containing, e.g., 1 mg/mL, 2 mg/mL, or 5 mg/mL vinca alkaloid in buffer containing, e.g., 100 or 200 mg/mL mannitol (obtainable from, e.g., SP Pharmaceuticals LLC, Albuquerque, NM; other excipients that are pharmaceutically acceptable, and in which the vinca alkaloid remains stable for extended periods, can also be used) and sodium acetate adjusted to pH 3.5 to 5.5, or preferably pH 4.5 to pH 4.7. One of the vials contains a solution containing liposomes comprising sphingomyelin and cholesterol (each of which is commercially available, e.g., from NEN Life Sciences, Avanti Polar Lipids, etc.) and suspended in a 300 mM citrate buffer at, e.g., pH 4.0. Another vial or vials contains a alkaline phosphate buffer (e.g., pH 9.0) such as dibasic sodium phosphate, 14.2 mg/ml (20 ml/vial).

In other preferred embodiments, a kit is used that contains 2 vials containing components that can be used to formulate the claimed liposome-encapsulated vinca alkaloid, e.g., vinorelbine, or a kit containing 1 vial containing a stable preparation of liposomes comprising pre-loaded vinca alkaloid. Such stable preparations can be accomplished in any of a number of ways, including, but not limited to, (1) a hydrated preparation stored at ambient temperatures or refrigerated and which contains one or more modifications or components to enhance chemical stability, e.g., antioxidants; (2) a hydrated preparation that was frozen and which includes a suitable excipient to protect from freeze/thaw-induced damage; or (3) a lyophilized preparation. Typically, any of the above-described kits also contain instructions for use as well as clean-up disposal materials.

In one method of preparing the liposomes, the vinca alkaloid and liposome solutions are each added to a sterile vial and mixed, at an appropriate concentration ratio, e.g., 0.01/1.0 to 0.2/1.0 (wt. vinca alkaloid/wt. lipid). The mixture is mixed, e.g., by inverting the vial multiple times. Following the formation of the liposomes in low pH buffer, and either before or after the sizing of the liposomes, the liposomes are introduced into buffer of a higher pH, e.g., a sodium phosphate buffer, thereby creating a pH gradient across the liposome surface. In preferred embodiments, the external environment of the liposomes is between about pH 7.0 and about pH 7.5. The liposomes and vinca alkaloids can be mixed for an amount of time sufficient to achieve the desired alkaloid/lipid ratio. The mixture can be mixed, e.g., by multiple inversions, and heated to temperatures between about 55° C. and about 80° C., preferably between about 60° C. and about 65° C., for about 5, 10, or more minutes. Such treatment causes greater than about 90% of the vinca alkaloid to become entrapped within the liposome.

In other embodiments, these steps are followed at a larger scale, and loaded liposomal vinca alkaloid, e.g., vinorelbine, is supplied to, e.g., a hospital pharmacy in ready-to-administer format. Such larger scale formulations may be prepared from different starting materials than those described for the kit; in particular, the buffers may be different.

An important characteristic of liposomal vinca alkaloids for pharmaceutical purposes is the drug to lipid ratio of the final formulation. As discussed earlier, drug:lipid ratios can be established in two ways: 1) using homogenous liposomes each containing the same drug:lipid ratio; or 2) by mixing empty liposomes with liposomes having a high drug:lipid ratio to provide a suitable average drug:lipid ratio. For different applications, different drug:lipid ratios may be desired. Techniques for generating specific drug:lipid ratios are well known in the art. Drug:lipid ratios can be measured on a weight to weight basis, a mole to mole basis or any other designated basis. Preferred drug:lipid ratios range from about 0.005:1 drug:lipid (by weight) to about 0.2:1 drug:lipid (by weight) and, more preferably, from about 0.1:1 drug:lipid (by weight) to about 0.3:1 drug:lipid (by weight).

Any of a number of methods can be used to load the vinca alkaloids and/or other drugs into the liposomes. Such methods include, e.g., an encapsulation technique and a transmembrane potential loading method. Generally, following such methods, the vinca alkaloids are present at about 0.1 mg/mL to about 0.5 mg/mL. Preferably, the vinca alkaloids are present at about 0.15 to 0.2 mg/mL.

VIII. Modulating Active Agent Release

The activity of many anticancer drugs is dependent on their pharmacokinetic behavior. This pharmacokinetic behavior defines the drug concentrations and period of time over which cancer cells are exposed to the drug. In the case of most anticancer drugs, longer exposure times are preferred as this results in increased killing of the cancer cells. In general, several parameters are used to describe drug pharmacokinetics. Plasma clearance half-time and area under the curve (AUC) are examples. The plasma clearance half-time is the time required for half of the administered drug to be removed from the plasma. The AUC is a measure of plasma drug levels over time and provides an indication of the total drug exposure. Generally, increased plasma clearance half-life and plasma AUC for an anticancer drug correlate with increased therapeutic efficacy.

The present invention describes methods and formulations for modulating drug release from liposomes. In one embodiment, the present invention provides a method for modulating the plasma circulation half-life of an active agent, comprising: (a) providing a liposome having free active agent and precipitated active agent encapsulated therein; and (b) varying the amount of the active agent that is precipitated in the liposome. Preferably, the "free active agent" and the "precipitated active agent" are the same active agent, however the present invention is not so limited. As used herein, the term "modulating" can mean either increasing or decreasing the release rate of the active agent from the liposomal carrier. For antineoplastic active agents, modulating is preferably decreasing or slowing the release rate of the active agent.

In preferred aspects, the liposomes of the present invention contain both encapsulated free active agent and precipitated active agent. The precipitate may be an amorphous precipitate. The amount of active agent that is precipitated within the liposome can be varied using a variety of mechanisms. For example, by varying the active agent to lipid ratio, the amount of active agent that is precipitated can be increased or decreased. Drug loading at low drug:lipid ratios, results in low concentrations of active agent (e.g., vinorelbine) in the liposome interior and hence most, if not all of the entire drug is in solution i.e., not precipitated or free. Low precipitation amounts result in a fast release rate of the drug from the liposome. Conversely, a high drug:lipid ratio results in high intraliposomal concentrations and high precipitation amounts. When the drug is in a precipitated form, subsequent release rates in vivo or in vitro are slow. For antineoplastic drugs (e.g., vinorelbine), slow release rates are preferable.

Without being bound by any particular theory, it is believed that the liposomes of the present invention undergo a "precipitation-dissolution mechanism" (PDM), which dictates drug release. In the PDM mechanism of the present invention, the dissolution rate of precipitated active agent (e.g., vinorelbine, vincristine, etc.) within the lipsomome's interior into the internal solution of the liposome is slow, compared to the rate of release of active agent out of the liposome to the exterior and is thus rate determining. That is, the rate of dissolution of the precipitated drug to free drug in the liposome's interior determines how fast the drug will be released into the plasma.

In certain embodiments, the active agent to lipid ratio can be varied by the addition of empty liposomes. In general, liposomes whether empty or those having active agents contained therein are cleared by cells of the reticuloendothelial system (RES). Typically, the RES will remove 80-95% of a dose of injected liposomes within one hour, effectively out-competing the selected target site for uptake of the liposomes. A variety of factors which influence the rate of RES uptake of liposomes have been reported including, liposome size, charge, degree of lipid saturation, and surface moieties. By including empty liposome vesicles, it is possible to shield the liposomes containing active agent from the RES. Thus, empty liposome vesicles actually extend the blood circulation lifetime of the liposomes by acting as "decoys". An extended circulation time is often needed for liposomes to reach the target region, cell or site from the site of injection. The empty liposomal vesicles keep the RES busy and as a result, the serum half-life of the liposomes having active agent contained therein is increased.

In certain other aspects, a component(s) is added to the liposome that will enhance the precipitation of the active agent. In this aspect, a variety of charged ions can be used to increase the amount of precipitated active agent in the vesicle's interior. In preferred aspects, divalent, trivalent or polyvalent anions are used. Suitable anions include, but are not limited to, carboxylate ($—CO_2^-$), sulfonate ($SO_3^-$), sulfate ($SO_4^{-2}$), hydroxide (—OH), alkoxides, phosphate ($—PO_4^{-2}$), and phosphonate ($—PO_3^{-2}$). Those of skill in the art will know of other components, which will enhance the amount of precipitated active agent in the liposome's interior.

Moreover, the drug:lipid ratios can be varied using the size of the liposome. The larger the liposome vesicle used, the smaller the drug:lipid ratio. In certain aspects, both the active agent to lipid ratio and the size of the liposome are varied to optimize the efficacy of the active agent.

The amount of encapsulated active agent that is precipitated in vesicle will vary and is somewhat dependent on the active agent itself. In certain embodiments, the amount of precipitated active agent is at least about 1% to about 95% (such as about 1%, 2%, 5%, 10%, 15%, 20%, 25%, 30%, 35%, 40%, 45%, 50%, 55%, 60%, 65%, 70%, 75%, 80%, 85%, 90% and 95% or any integer value between these values) of total active agent. For topotecan, the amount of the precipitated active agent encapsulated in the liposome is at least 50% of the total active agent. For vinorelbine, the amount of the precipitated active agent encapsulated in the liposome is at least 1%, 2%, 5%, 10%, 20%, or 50%, or any integer value between) of the total active agent.

The concentration of free active agent within a liposome of the invention may also vary, depending, in part, upon the active agent and the amount of active agent that precipitates within the liposome. In general, the concentration of free active agent will be lower when more of the active agent precipitates within the liposome. Accordingly, the invention provides liposomal compositions comprising varying concentrations of free active agent within the liposome. In certain embodiments, the concentration of free active agent is greater than 1 mM. In particular embodiments, the concentration of free active agent is between 1 mM and 100 mM. In other embodiments, the concentration of free active agent is less than 1 mM, less than 10 mM, less than 20 mM, or less than 100 mM.

In preferred aspects, when the active agent is an antineoplastic drug, using higher drug:lipid ratios results in higher amounts of encapsulated precipitated drug. As a result, drug release from the liposomes in vivo is slower than for similar compositions prepared at lower drug:lipid ratio. These higher drug:lipid ratio liposomes exhibit extended plasma half-life and increased plasma AUC values. Advantageously, these formulations exhibit improved antitumor efficacy.

In certain embodiments, the ratio of active agent:lipid is about 0.005-1:1 (w/w). Preferably, the ratio of active agent: lipid is about 0.05-0.9:1 (w/w) and more preferably, the ratio of active agent:lipid is about 0.1-0.5:1 (w/w). In certain preferred embodiment, the ratio of active agent:lipid is 0.1-0.3 (w/w). By modulating the plasma circulation half-life of the active agent, it is thus possible to maximize or optimize efficacy of the active agent.

IX. Targeting Liposomes

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044, the teachings of which are incorporated herein by reference). The targeting moieties can comprise the entire protein or fragments thereof.

Targeting mechanisms generally require that the targeting agents be positioned on the surface of the liposome in such a manner that the target moiety is available for interaction with the target, for example, a cell surface receptor. The liposome is designed to incorporate a connector portion into the membrane at the time of liposome formation. The connector portion must have a lipophilic portion that is firmly embedded and anchored into the membrane. It must also have a hydrophilic portion that is chemically available on the aqueous surface of the liposome. The hydrophilic portion is selected so as to be chemically suitable with the targeting agent, such that the portion and agent form a stable chemical bond. Therefore, the connector portion usually extends out from the liposomal surface and is configured to correctly position the targeting agent. In some cases, it is possible to attach the target agent directly to the connector portion, but in many instances, it is more suitable to use a third molecule to act as a "molecular bridge." The bridge links the connector portion and the target agent off of the surface of the liposome, thereby making the target agent freely available for interaction with the cellular target.

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci. (USA)*, 87:2448-2451 (1990). Other examples of antibody conjugation are disclosed in U.S. patent application Ser. No. 08/316,394, filed Sep. 30,1994, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes*, 149 *Methods in Enzymology* 111-119 (Academic Press, Inc. 1987)). Other targeting methods include the biotin-avidin system.

X. Administration of Lipid-Encapsulated Vinca Alkaloids

Liposome-encapsulated vinca alkaloids can be administered in any of a number of ways, including parenteral, intravenous, systemic, local, oral, intratumoral, intramuscular, subcutaneous, intraperitoneal, inhalation, or any such method of delivery. Preferably, the pharmaceutical compositions are administered parenterally, i.e., intraarticularly, intravenously, intraperitoneally, subcutaneously or intramuscularly. More preferably, the pharmaceutical compositions are administered by intravenous drip or intraperitoneally by a bolus injection. In one embodiment, a patient is given an intravenous infusion of the liposome-encapsulated vinca alkaloids (single agent) through a running intravenous line over, e.g., 5-10 minutes, 15-20 minutes, 30 minutes, 60 minutes, 90 minutes, or longer. In one embodiment, a 60 minute infusion is used. In other embodiments, an infusion ranging from 6-10 or 15-20 minutes is used. Such infusions can be given periodically, e.g., once every 1, 3, 5, 7, 10, 14, 21, or 28 days or longer, preferably once every 7-21 days, and preferably once every 7 or 14 days. As used herein, each administration of a liposomal vinca alkaloid is considered one "course" of treatment.

The concentration of liposomes in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration can be increased to lower the fluid load associated with treatment. Alternatively, liposomes composed of irritating lipids can be diluted to low concentrations to lessen inflammation at the site of administration. The amount of liposomes administered will depend upon the particular camptothecin used, the disease state being treated and the judgement of the clinician, but will generally, in a human, be between about 0.01 and about 50 mg per kilogram of body weight, preferably between about 5 and about 40 mg/kg of body weight. Higher lipid doses are suitable for mice, for example, 50-120 mg/kg.

Suitable formulations for use in the present invention can be found, e.g., in *Remington's Pharmaceutical Sciences*, Mack Publishing Company, Philadelphia, Pa., 17$^{th}$ Ed. (1985). Often, intravenous compositions will comprise a solution of the liposomes suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. These compositions can be sterilized by conventional sterilization techniques, such as filtration. The resulting aqueous solutions may be packaged for use or filtered under aseptic conditions and lyophilized, the lyophilized preparation being combined with a sterile aqueous solution prior to administration. The compositions may also contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the composition may include lipid-protective agents, which protect lipids against free-radical and lipid-peroxidative damages on storage. Lipophilic free-radical quenchers, such as a.-tocopherol and water-soluble iron-specific chelators, such as ferrioxamine, are suitable. The concentration of liposomes in the carrier can vary. Generally, the concentration will be about 20-200 mg/mL. However, persons of skill can vary the concentration to optimize treatment with different liposome components or for particular patients. For example, the concentration may be increased to lower the fluid load associated with treatment.

The amount of vinca alkaloids administered per dose is selected to be above the minimal therapeutic dose but below a toxic dose. The choice of amount per dose will depend on a number of factors, such as the medical history of the patient, the use of other therapies, and the nature of the disease. In addition, the amount of vinca alkaloid administered may be adjusted throughout treatment, depending on the patient's response to treatment and the presence or severity of any treatment-associated side effects. In certain embodiments, the dosage of liposomal vinca alkaloid or the frequency of administration is approximately the same as the dosage and schedule of treatment with the corresponding free drug. However, it is understood that the dosage may be higher or more frequently administered as compared to free drug treatment, particularly where the liposomal formulation exhibits reduced toxicity. It is also understood that the dosage may be lower or less frequently administered as compared to free drug treatment, particularly where the liposomal formulation exhibits increased efficacy as compared to the free drug.

In certain embodiments, an initially low dose will be given, which can be increased based on the response and/or tolerance of the patient to the initial dose. For example, 0.5, 1.0, 1.5, 2.0, 2.4, 5.0, 10.0, 15.0, 20.0, 25.0, 25.0, 30.0, 50.0, 100.0 mg/m$^2$ (i.e., mg vinca alkaloid, e.g., vincristine, per m$^2$ body surface area) or higher concentrations can be administered. In one embodiment, patients are administered a liposomal vincristine dose of 2.0 mg/m$^2$, corresponding to a lipid dose of about 40 mg/m$^2$ or about 1.1 mg/kg lipid and 0.05 mg/kg vincristine for an average 70 kg patient, or about 3 mg to about 6 mg vincristine per dose.

Patients typically will receive at least 2 courses of such treatment, and potentially more, depending on the response of the patient to the treatment. In single agent regimens, total courses of treatment are determined by the patient and physician based on observed responses and toxicity. Up to 12 courses of treatment, once every 14 days, have demonstrated satisfactory patient responses for certain vinca alkaloids. Greater numbers may be warranted in certain cases. Similarly, the number of courses of treatment using lipo-CHOP will be determined by the patient and physician.

Because vincristine dosages are limited by neurotoxicity in humans, it is sometimes useful to co-administer liposomal vincristine with a treatment for neurotoxicity. This treatment may be prophylactic or therapeutic. An example is the administration of Neurontin™ gabapentin (Parke-Davis), or neurotonin, for treatment of neuropathic pain, e.g., 100-200 mg Neurontin™ is administered 3 times per day to an adult patient. If neuropathic pain improves, then liposomal vincristine treatments may continue. Because this type of prophylactic or therapeutic treatment is intended only to treat side-effects of liposomal vincristine, it is considered separately from the combination therapies set forth below.

As described supra generally, liposomal vinorelbine may be administered at doses comparable to those used for free vinorelbine, which is associated with an initial single-agent dose of 30 mg/m$^2$ administered weekly. The recommended method of administration of free vinorelbine is an intravenous injection over 6-10 minutes. Single agent vinorelbine, free or liposomal, may be given, e.g., weekly, until progression or dose limiting toxicity. Free vinorelbine is administered in combination with other chemotherapeutic agent, including, e.g., cisplatin, weekly at a dose of 25 mg/m$^2$. In addition, liposomal vinorelbine may be administered at higher or lower doses and alternative schedules, including those indicated supra for liposomal vinca alkaloids.

This invention is based in part on the surprising discovery that, in contrast to free form vinca alkaloids, liposome-encapsulated vinca alkaloids can be administered without a cap on the total dosage. For example, whereas free form vincristine is typically administered with a cap of 2.0 mg, liposome-encapsulated vincristine can be administered at a constant dosage of, preferably, 2.0 mg/m$^2$. Thus, for a typical patient of from 1.5 to 3.0 m² surface area, a dose of from about 3.0 to about 6.0 mg vincristine can be administered.

Exemplary dosages and treatment for a variety of chemotherapy compounds are known and available to those skilled in the art and are described in, e.g., Physician's Cancer Chemotherapy Drug Manual, E. Chu and V. Devita (Jones and Bartlett, 2002), which is incorporated by reference in its entirety.

XI. Combination Therapies

In numerous embodiments, liposome-encapsulated vinca alkaloids will be administered in combination with one or more additional compounds or therapies, such as surgery, radiation treatment, or chemotherapy. For example, multiple vinca alkaloids can be co-administered, or one or more vinca alkaloids can be administered in conjunction with another therapeutic compound, such as cyclophosphamide, doxorubicin, prednisone, other alkaloids such as the taxanes, camptothecins, and/or podophyllins, other chemotherapeutic agents such as antisense drugs or anti-tumor vaccines.

In such embodiments, the liposome-encapsulated vinca alkaloids can be used alone or in combination with other chemotherapeutic agents, including any approved oncology drug. Examples of approved oncology drugs that may be used in combination with a liposomal drug formulation of the invention include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine with Polifeprosan 20 Implant, CCNU, celecoxib, chlorambucil, cisplatin, cisplatin-epinephrine gel, cladribine, cyclosporin A, cytarabine liposomal, cytosine arabinoside, daunorubicin liposomal, cytoxan, daunorubicin, dexrazoxane, dodetaxel, doxorubicin, doxorubicin liposomal, DTIC, Elliott's B Solution, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, liposomal daunorubicin, litretinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, rituxan, streptozocin, STI-571, talc, tamoxifen, taxotere, temozolamide, teniposide, VM-26, topotecan (Hycamtin), toremifene, tretinoin, ATRA, valrubicin, velban, vinblastine, vincristine, VP16, and vinorelbine.

In one embodiment, liposome encapsulated vincristine is used along with cyclophosphamide, doxorubicin, and prednisone, thereby forming an improved, liposomal CHOP formulation ("lipo-CHOP").

In other embodiments, liposomal vinorelbine is used in combination with one or more other chemotherapeutic agents, such as Gemcitabine or taxol or derivatives thereof. Combination therapies including vinorelbine have been demonstrated to have increased efficacy as compared to single drug treatment, in certain cases. For example, vinorelbine is associated with promising six-month and median survival rates in women with ovarian cancer that has relapsed following treatment with a platinum and paclitaxel, and the combination of vinorelbine and cisplatin has shown superior results in terms of response rates and survival when compared to single-agent cisplatin. Wozniak, A. J. et al., *J. Clin. Oncol.* 16:2459-2465 (1998).

In certain embodiments, multiple compounds are loaded into the same liposomes. In other embodiments, liposome-encapsulated vinca alkaloids are formed individually and subsequently combined with other compounds for a single co-administration. Alternatively, certain therapies are administered sequentially in a predetermined order, such as in CHOP or lipo-CHOP. Liposome-encapsulated vincristine can also be formulated in a CVP combination, or cyclophosphamide-vincristine-prednisone.

Liposome-encapsulated vinca alkaloids can also be combined with anti-tumor agents such as monoclonal antibodies including, but not limited to, Oncolym™ (Techniclone Corp. Tustin, Calif.) or Rituxan™ (IDEC Pharmaceuticals), Bexxar™ (Coulter Pharmaceuticals, Palo Alto, Calif.), or IDEC-Y2B8 (IDEC Pharmaceuticals Corporation). In addition, liposome-encapsulated vinca alkaloids can be administered along with one or more non-molecular treatments such as radiation therapy, bone marrow transplantation, hormone therapy, surgery, etc.

In a preferred embodiment, liposome encapsulated vinca alkaloids are administered in combination with an anti-cancer compound or therapy which provides an increased or synergistic improvement in tumor reduction based on mechanism of action and non-overlapping toxicity profiles. In particular, liposomal vinca alkaloids can be delivered with a taxane, which optionally may also be a liposomal taxane. While it is thought that vinca alkaloids depolymerize microtubules and taxanes stabilize microtubules, the two compounds have been found to act synergistically in the impairment of tumor growth, presumably because both are involved in the inhibition of microtubule dynamics. See, Dumontet, C. and Sikic, B. I. (1999) *J. Clin Onc.* 17(3) 1061-1070. Liposomal formulations of the vinca alkaloids according to the present invention will thus significantly diminish the myeloid and neurologic toxicity associated with the sequential administration of free form vinca alkaloids and taxanes.

Other combination therapies known to those of skill in the art can be used in conjunction with the methods of the present invention.

EXAMPLES

The following examples are offered to illustrate, but no to limit the claimed invention.

Example 1

Preparation of Liposome-Encapsulated Vincristine

Liposome-encapsulated vincristine (Vincristine Sulfate Liposome Injection) was prepared using a six vial kit. Vials 1 and 2 contained a vincristine sulfate solution (1 mg/mL Vincasar PFS®, SP Pharmaceuticals LLC, Albuqueque, N. Mex.) in buffer comprising mannitol and sodium acetate, pH 4.5-4.7, vial 3 contained empty liposomes (100 mg/mL Sphingomyelin/Cholesterol liposomes, at a ratio of between about 60/40 to 50/50, or more preferably 55/45 mol %/mol %) in buffer comprising 300 mM citrate at pH 4.0, vials 4 and 5 contained an alkaline phosphate buffer (14.2 mg/mL dibasic sodium phosphate hepta hydrate), and vial 6 was an empty, sterile vial. The foregoing empty liposomes were prepared using thin film hydration and standard extrusion techniques, as described in U.S. Pat. No. 5,741,516.

4 mL of Vincristine Sulfate was removed from vials 1 and 2 and added to sterile vial 6. Subsequently, 0.8 mL sphingomyelin/cholesterol liposomes was removed from vial 3 and added to vial 6. Vial 6 was inverted five times to mix the materials. 20 mL of the sodium phosphate solution from vials 4 and 5 was added to vial 6. Vial 6 was again inverted five times, without shaking, to mix the materials. Vial 6 was then heated in a water bath at 60-65° C. for five minutes, after which the vial was again inverted five times. The vial was then again heated for five minutes and inverted five more times.

The final product contained 0.16 mg/mL vincristine sulfate and 3.2 mg/mL total lipid.

Example 2

Liposome-Encapsulated Vincristine in Relapsed NHL Methods 50 patients with relapsed non-Hodgkin's Lymphoma (NHL), and 1 with Adult Lymphoblastic Lymphoma (ALL), were included in the study. Each patient was at least 16 years of age, did not have HIV or any other serious infection, did not have any disease of the central nervous system, and had normal renal function and neutrophils at least 0.5K, and platelets at least 50K. Each patient received up to 12 doses of 2.0 mg/m$^2$ of intravenous liposomal-vincristine administered once every 14 days. The liposomes used comprised sphingomyelin and cholesterol.

Results 35 of the 51 patients were evaluated. The median age of these 35 patients was 62 years (range 19-86), and 21 of the patients were male. 12 of the patients had follicular NHL, 7 had transformed, 11 diffuse large cell, 3 mantle cell, 1 NK cell, and one ALL. Clinical grade was high in 1, aggressive in 17, indolent in 10, and transformed in 7 patients. Serum LDH was high in 16 out of the 35 patients, and B2 microglobulin greater than 3.0 mg/L in 19 out of 30 patients. The median number of prior therapeutic regimens was 3 (range 1-10). 18 of the 35 patients were refractory to the regimen immediately preceding the liposome-encapsulated vincristine. All 35 had previously received vincristine administration. For the 34 patients with NHL, 14 patients exhibited a complete or partial response, for an overall response rate of 40% (95% confidence interval: 24%-58%). Responses according to clinical grade was as shown in Table 1.

TABLE 1

|  | Indolent | Transformed | Aggressive | Transformed or Aggressive |
|---|---|---|---|---|
| # Patients | 10 | 7 | 17 | 24 |
| # Responders (complete or partial response) | 1 | 5 | 8 | 13 |
| % Complete or partial response | 10 | 71 | 47 | 54 |
| 95% Confidence Interval | 1-45 | 29-96 | 23-72 | 33-74 |

Conclusions

Median response duration was 4 months. The fact that half of the responding patients maintain the response for at least 4 months after treatment is a surprising, unexpected and clinically impressive response for a heterogeneous group of patients who previously would have been given a very poor prognosis.

The above results demonstrate that full doses of liposomal vincristine can be given in relapsed NHL with good activity, even in heavily pretreated populations.

In addition, liposomal vincristine demonstrated significantly less non-specific toxicity than free vincristine. Peripheral neurotoxicity is the most frequent and dose-limiting toxic effect of free vincristine. Peripheral neuropathic effects usually begin in adults who receive a total dose of 5 to 6 mg (2-3 doses of free vincristine) and are generally significant after a cumulative dose of 15-20 mg (8-10 doses of free vincristine). Significantly, in the present study, a typical patient received 3-5 mg in one dose alone, and cumulative doses of up to 37 mg were delivered, with no patient reporting significant liposomal vincristine-induced peripheral neurotoxicity. Even higher total doses are likely to be tolerated. These higher doses are highly desirable for the management of NHL, and represent a significant and surprising step forward in the treatment of this disease.

Example 3

Use of Liposomal Vinca Alkaloids as First-Line Treatment for Lymphomas

This example illustrates the use of liposomal vinca alkaloids as a first-line treatment, in combination with other chemotherapeutics, for treatment of patients presenting with lymphomas, particularly non-Hodgkin's lymphoma (low-grade or intermediate-grade). Patients presenting with transformed or aggressive NHL may receive this improved combination treatment as a first-line treatment, or the physician may prefer single agent OncoTCS™ treatment as described in the previous examples. The combination therapy regimen set out below takes advantage of the surprising result that much higher doses of vincristine can be administered when delivered in the liposomes of the present invention, with greatly reduced toxicity.

The preferred combination regimen is an improved CHOP regime ("Lipo-CHOP") comprising: Cyclophosphamide, Hydroxydaunorubicin (doxorubicin), OncoTCS™, and Prednisone. One treatment cycle takes about 5 days, and cycles are repeated about every 21-28 days. An exemplar cycle consists of Cyclophosphamide (750 mg/m$^2$IV, d 1)

Hydroxydaunorubicin (50 mg/m$^2$IV, d 1)

OncoTCS™ (2.0 mg/m$^2$IV, d 1, (no cap necessary))

Prednisone (100 mg PO qd×5 day)

Treatments are conducted with the same nursing interventions required for standard CHOP treatment.

Patients receiving the improved CHOP treatment are expected to show significant improvement over standard CHOP in partial and complete remission rates, period of remission/time to relapse after treatment, and median survival times.

Example 4

Treatment of Lymphomas with Single Agent Liposomal Vincristine

In a further study, 50 human patients presenting with different classes of lymphoma were treated with single agent liposomal vincristine, as described in Example 2. Results were as indicated in Table 2.

TABLE 2

| | First Relapse from CR | Primary Refractory | Post-ABMT | ≧2 Relapses | Multicenter Study Population* |
|---|---|---|---|---|---|
| Number of Patients Evaluable | 11 | 11 | 10 | 26 | 36 |
| # CR | 4 | 0 | 0 | 0 | 0 |
| # PR | 4 | 0 | 2 | 10 | 12 |
| Overall Response Rate (%) | 73 | 0 | 20 | 38 | 33 |
| 95% Confidence Intervals (%) | 39 to 95 | 0 to 28 | 1 to 32 | 20 to 59 | |

18% grade 3 to 4 neurotoxicity; no toxic deaths.
CR = Complete response
PR = Partial response
Primary refractory means that no response to initial treatment was observed.
ABMT = Autologous bone marrow transplant Again, these results show that single agent treatment of liposomal vincristine is an excellent treatment for lymphomas. These results strongly suggest a role for liposomal vincristine in Lipo-CHOP and for single agent first line treatment of lymphomas.

Example 5

Additional Studies

FIG. 1 provides results for a clinical trial using the herein-described methods, which demonstrates that the present methods are particularly effective in the treatment of indolent, transformed, relapsed, and aggressive post bone-marrow transplant (BMT) forms of non-Hodgkin's Lymphoma.

Example 6

Response to Liposomal Vincristine Per Prior Regimen Number

FIG. 2 provides results showing the number of evaluable patients with relapsed aggressive NHL, the number of such patients that exhibited a complete response or remission (CR), the number that exhibited a partial response or remission (PR), the percentage that exhibited either a CR or a PR, and the 95% confidence interval for each percentage value. These data are presented for patients who have received one prior treatment, two or more prior treatments, and, of the latter category, those who responded to the treatment immediately prior to the study and those who did not respond to the previous treatment.

This study demonstrates that the present methods are unusually effective for treating each category of patients.

Example 7

Preparation of Liposomal Vinorelbine

Magnesium-loaded ESM/CH (55/45) vesicles containing the non-exchangeable and non-metabolized radiolabed [$^{14}$C]-CHE were prepared by the ethanol injection method. Vinorelbine was mixed with trace amounts of [$^3$H]-vinorelbine and was encapsulated in these vesicles at initial D/L ratios 0.1, 0.2 and 0.3 (w/w) using an ionophore (A23187)-mediated loading technique as described in Fenske et al., Biochim. Biophys. Acta (1998). The non-encapsulated drug and ionophore were removed by dialysis for 48 h against phosphate buffered sucrose (10 mM phosphate/300 mM sucrose pH 7). Drug and lipid concentrations of the dialyzed preparations were determined and the formulations were diluted to a lipid concentration of 5 mg/ml.

Example 8

Retention and Release of Liposomal Vinorelbine

The clearance and drug leakage characteristics of liposomal vinorelbine formulations were determined in mice as described below and in Table 3.

TABLE 3

Pharmacokinetics and Release of Vinorelbine from ESM:CH Liposomes

| | Injected Dose (mg/kg) | | | |
|---|---|---|---|---|
| Formulation | Drug | Lipid | D/L Ratio | Vesicle Size (nm) |
| D/L 0.1 | 7.6 | 100 | 0.08 | 112 ± 33 |
| D/L 0.2 | 18.8 | 100 | 0.19 | 119 ± 47 |
| D/L 0.3 | 22.7 | 100 | 0.23 | 118 ± 45 |

Liposomal vinorelbine formulations were prepared as described in Example 7. Formulations diluted to a lipid concentration of 5 mg/ml were injected i.v. into ICR mice at a lipid dose of 100 mg/kg. The injected dose of vinorelbine varied between 7.6 and 22.7 mg/kg depending on the final D/L ratio of the formulation tested. Four mice were used per time point. At various times after treatment, mice were anesthetized with a mixture of ketamine and xylazine. Blood was obtained by cardiac puncture and collected in EDTA coated microtainer tubes. Aliquots of the blood were taken for measurement of lipid and vinorelbine by dual label liquid scintillation counting. For measurement of plasma lipid and drug concentrations, the residual blood samples were centrifuged for 10 min at 1000 g and aliquots of the resulting plasma were collected for analysis. The blood clearance rates of liposomal vinorelbine are summarized in Table 4.

TABLE 4

Blood Clearance of Liposomal Vinorelbine in ICR Mice (up to 8 h Post Injection)

| Formulation | Injected Dose (mg/kg) Drug | Injected Dose (mg/kg) Lipid | D/L Ratio | Half-life t½ [r²]* (hours) Drug Clearance | Half-life t½ [r²]* (hours) Lipid Clearance | Half-life t½ [r²]* (hours) Drug Release |
|---|---|---|---|---|---|---|
| D/L 0.1 | 7.6 | 100 | 0.08 | 0.8 (0.98) | 5.8 (0.97) | 2.0 (0.98) |
| D/L 0.2 | 18.8 | 100 | 0.19 | 2.0 (0.99) | 5.4 (0.99) | 5.1 (0.99) |
| D/L 0.3 | 22.7 | 100 | 0.23 | 3.0 (0.99) | 4.9 (0.99) | 14.3 (0.98) |

*The half-lives (t ½) in hours for the removal of vesicles and encapsulated vinorelbine from blood and for the release of encapsulated drug from circulating vesicles were calculated from the linear regression of the ln (% Remaining) vs time plots. The $r^2$ values for these regressions are given in brackets.

Figure 4A:
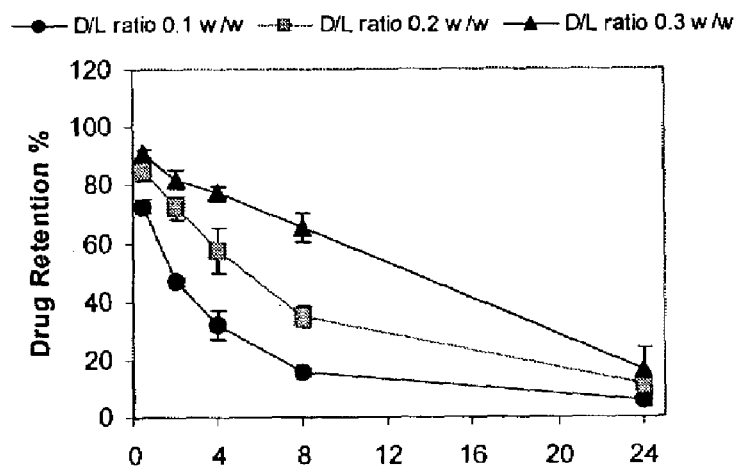
FIGS. 4A-C shows the pharmacokinetic behavior of a liposomal formulation of vinorelbine. Panel A shows the rates of drug leakage from circulating carriers for three formulations of differing drug:lipid ratio (0.1:1, 0.2:1, 0.3:1). Vinorelbine was encapsulated at different D/L ratio in ESM:CH vesicles using the ionophore procedure. Liposomal vinorelbine was administered at a lipid dose of 50 mg/kg. The data (±s dev) are average values from four mice. Drug release is dependent upon drug:lipid ratio with the slowest rate of release seen for the highest ratio (0.3:1). Panel B shows lipid recovery in the blood. Panel C shows that modulation in drug release rates from the carrier results in changes to the blood clearance half-life for vinorelbine.
Figure 4B:
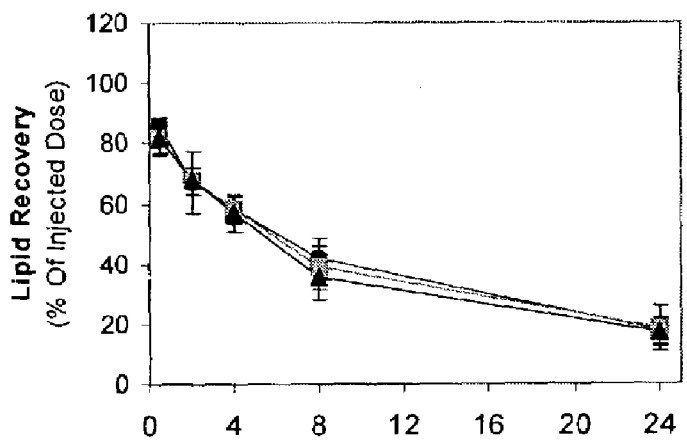
Figure 4C:
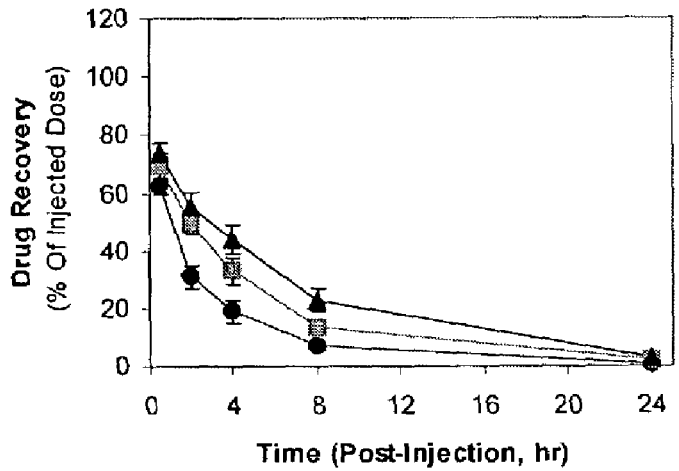
Figure 5A:
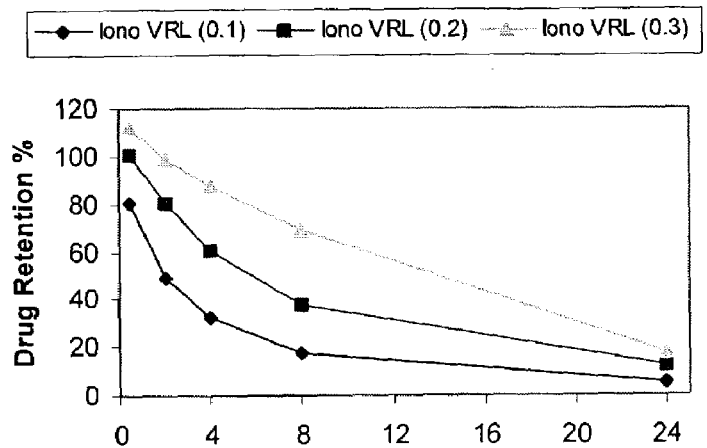
FIGS. 5A-C shows the pharmacokinetic behavior of a liposomal formulation of vinorelbine when plasma drug levels are used to follow pharmacokinetics. Panel A shows drug retention versus time. Panel B shows lipid recovery versus time. Panel C shows drug recovery versus time.
Figure 5B:
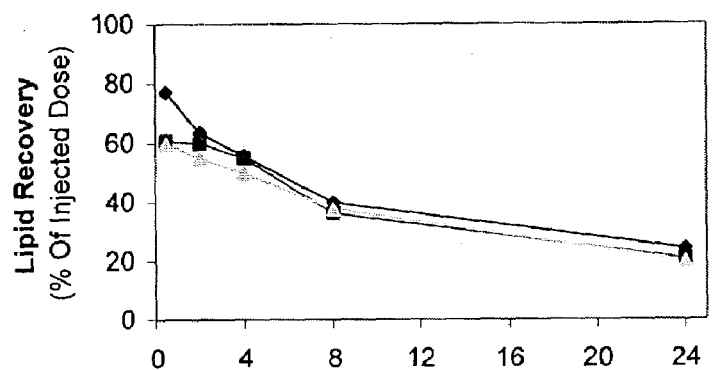
Figure 5C:
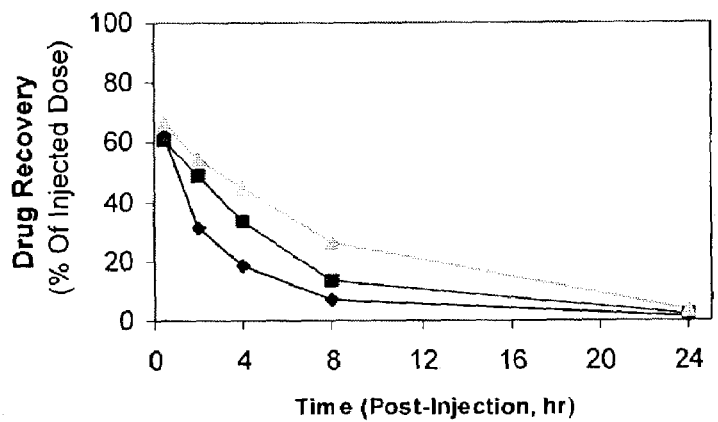

The concentrations of vinorelbine in the blood and plasma were significantly dependent on the D/L ratios of the injected formulations, as illustrated in FIGS. 4 and 5. At all time points, the amount of drug recovered in the blood was lowest for the liposome formulation with a D/L ratio of 0.1 (FIG. 4, bottom). For this formulation, 19% of the injected encapsulated drug was recovered at 4 h compared to 36% and 44% for formulations with D/L ratios of 0.2 and 0.3, respectively. The circulation half-lives of encapsulated vinorelbine in the blood were 0.8 h, 2.0 h, and 3.0 h for the 0.1, 0.2 and 0.3 D/L ratio formulations respectively (Table 4).

The low level of vinorelbine in the blood following administration of the low D/L ratio (0.1) liposome formulation was a result of increased drug leakage (FIG. 4, top). Drug retention was lowest at the 0.1 D/L ratio and highest for the 0.3 D/L ratio formulation. For the 0.3 D/L ratio, 79% of the encapsulated vinorelbine remained in the liposomes at 4 h, 65% at 8 h and 20% at 24 h after injection. Vinorelbine release from the 0.3 D/L ratio formulation was linear over the 24-hour period and had a release half-life of 14.3 h (Table 4).

A liposomal vinorelbine formulation with appropriate pharmacokinetics has been achieved. The retention of encapsulated vinorelbine in ESM:CH vesicles following intravenous administration in mice was dependent on the drug-to-lipid ratio of the formulations, with formulation having higher D/L ratios showing better drug retention. Liposomal vinorelbine (D/L ratio 0.3, w/w) exhibited sustained drug release in vivo with 20% of the encapsulated released at 4 h, 40% at 8 h and 80% at 24 h. These characteristics fulfilled desired criteria for circulation times and release rates of liposomal anticancer formulations.

Example 9

Retention and Release of Liposomal Vinblastine

The clearance and drug leakage characteristics of liposomal vinblastine formulations were determined essentially as described for liposomal vinorelbine in Example 8. Magnesium-loaded ESM/CH (55/45) vesicles containing the non-exchangeable and non-metabolized radiolabed [$^{14}$C]-CHE were prepared by the ethanol injection method. Vinblastine mixed with trace amounts of [$^3$H]-vinblastine was encapsulated at different D/L ratios (0.1, 0.2, and 0.3 w/w) in ESM:CH vesicles using the ionophore procedure. The effect of D/L ratio was investigated after administration of liposomal vinblastine formulations at a lipid dose of 100 mg/kg lipid. At various times following administration, mice were anesthetized with Ketamine/Xylazine and blood was collected by cardiac puncture. Blood was aliquoted into EDTA vacutainer tubes, and 50 μl of whole blood sample was removed for liquid scintillation analysis. Plasma was collected by centrifugation (1500 rpm for 10 minutes), and an aliquot was analyzed by liquid scintillation analysis. Blood and plasma samples were analyzed for lipid and drug content by dual label liquid scintillation counting.

Figure 6A:
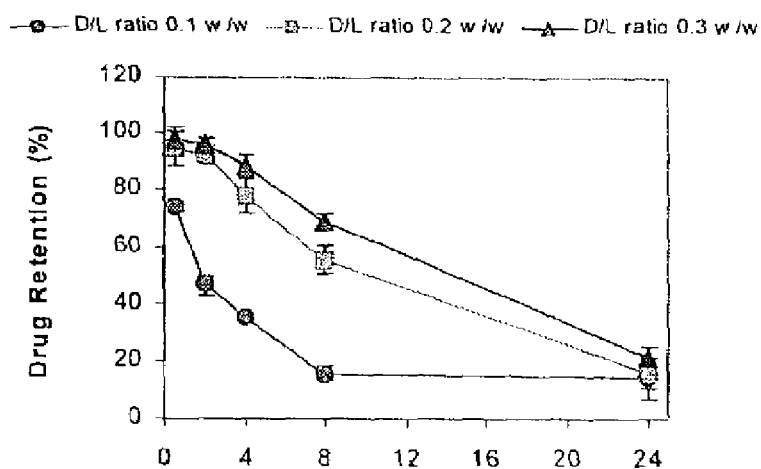
FIGS. 6A-C shows the pharmacokinetic behavior of formulations of liposomal vinblastine as a function of drug:lipid ratio (blood PK). Vinblastine was encapsulated at different D/L ratios in ESM:CH vesicles using the ionophore procedure. Liposomal vinblastine formulations were administered at a lipid dose of 50 mg/kg. Drug leakage from the liposomal carrier is determined by the initial drug:lipid ratio with slower release for formulations of higher drug ratio. Panel A shows drug retention versus time. Panel B shows lipid recovery versus time. Panel C shows drug release rates correlate with changes to drug clearance half-life from the blood.
Figure 6B:
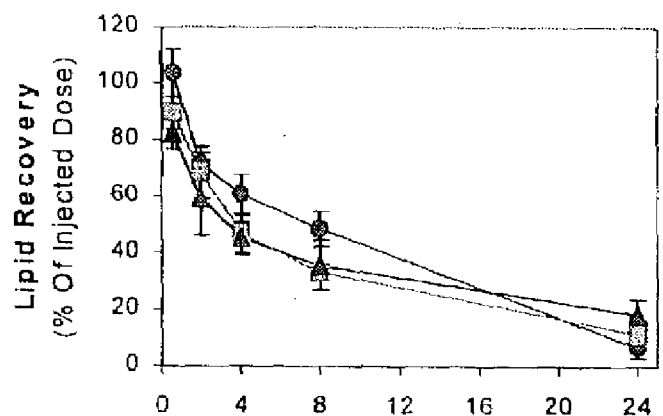
Figure 6C:
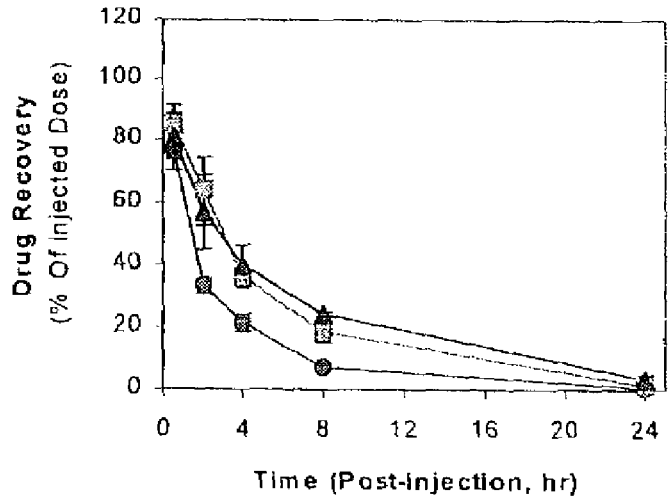
Figure 7A:
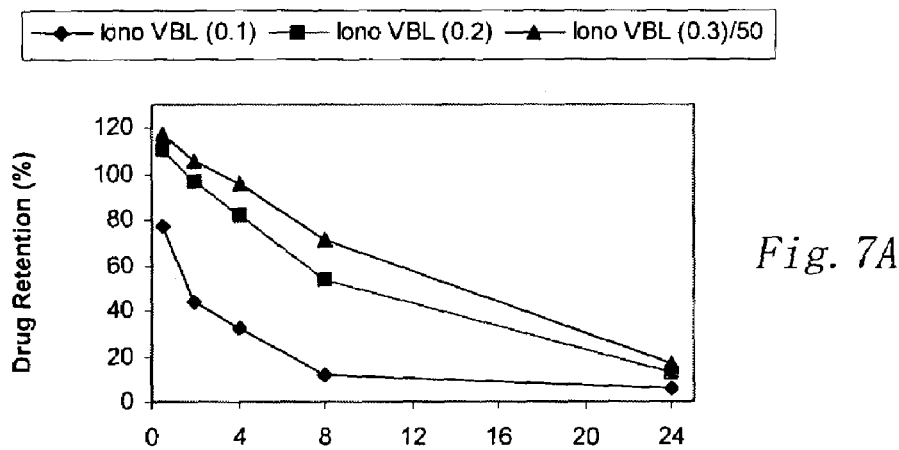
FIGS. 7A-C shows the pharmacokinetic behavior of formulations of liposomal vinblastine as a function of drug:lipid ratio (plasma PK). Panel A shows drug retention versus time. Panel B shows lipid recovery versus time. Panel C shows drug release rates correlate with changes to drug clearance half-life from the plasma.
Figure 7B:
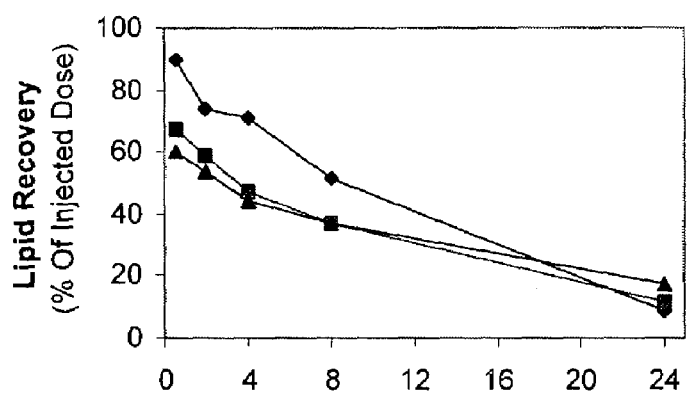
Figure 7C:
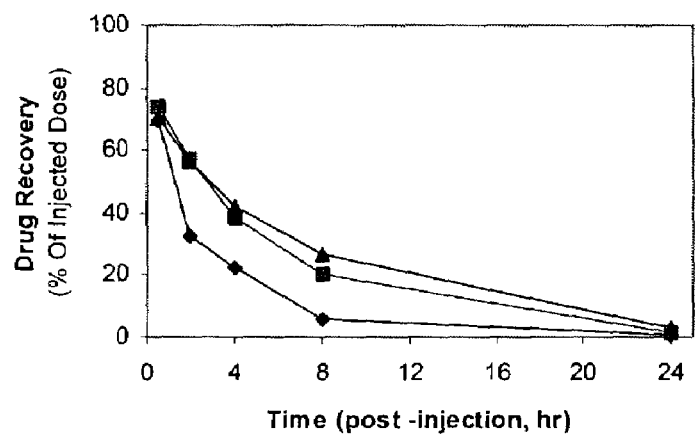

The concentrations of vinblastine in the blood and plasma were significantly dependent on the D/L ratios of the injected formulations, as illustrated in FIGS. 6 and 7. At all time points, the amount of drug recovered in the blood was lowest for the liposome formulation with a D/L ratio of 0.1 (FIG. 4, bottom).

Figure 8A:
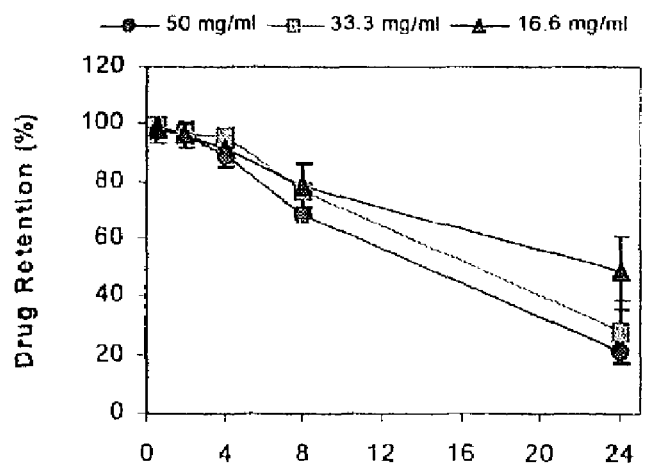
FIGS. 8A-C shows the influence of lipid dose on PK behavior (blood PK). Liposomal vinblastine formulations were administered at a drug:lipid ratio of 0.3:1 and lipid doses of 50, 33.3 and 16.6 mg/kg. The data (±s dev) are average values from four mice. As illustrated therein, similar rates of drug release (A), lipid clearance (B) and drug clearance (C) are seen for a liposomal vinblastine formulation of drug:lipid ratio 0.3:1 over a lipid dose range of 16.6 mg/kg to 50 mg/kg.
Figure 8B:
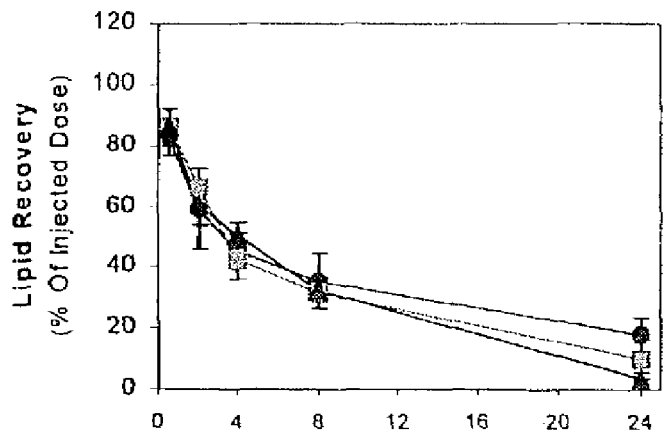
Figure 8C:
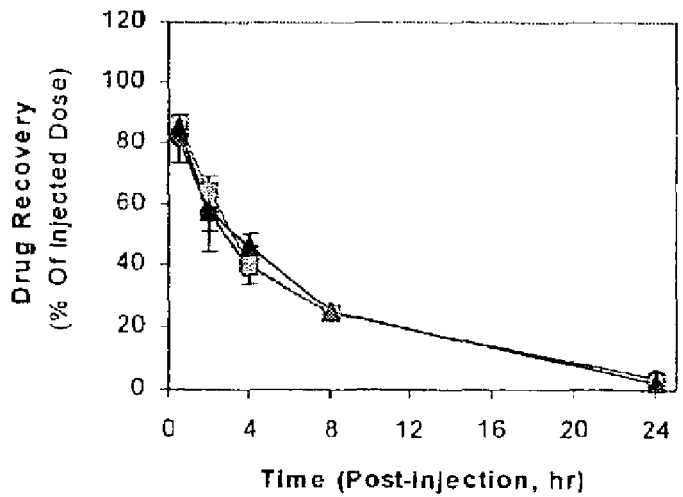
Figure 9A:
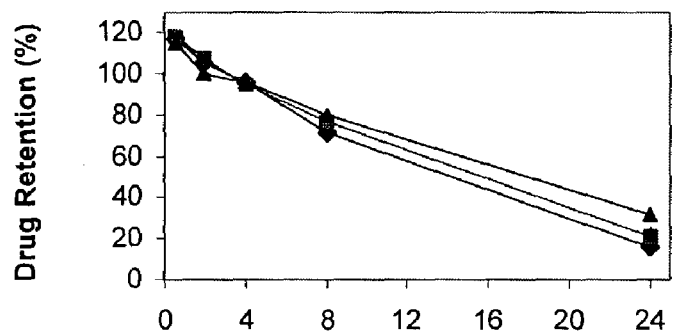
FIGS. 9A-C shows the influence of lipid dose on PK behavior (plasma PK). As illustrated therein, similar rates of drug release (A), lipid clearance (B) and drug clearance (C) are seen for a liposomal vinblastine formulation of drug:lipid ratio 0.3:1 over a lipid dose range of 16.6 mg/kg to 50 mg/kg.
Figure 9B:
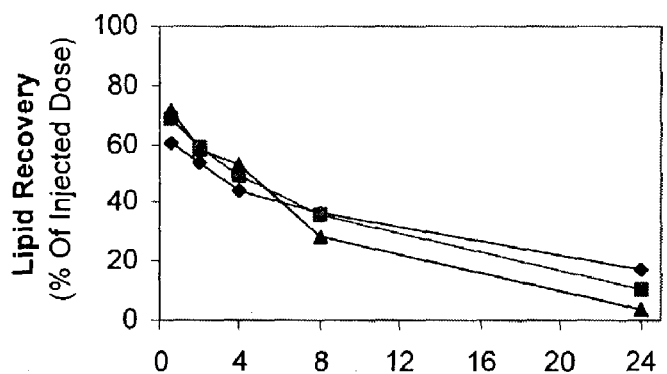
Figure 9C:
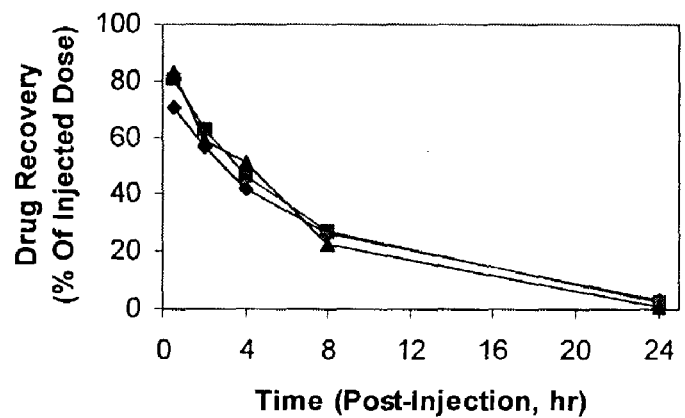

To determine the effect of lipid dose, the 0.3 D/L ratio liposomal vinblastine was injected at 50, 33.3 and 16.6 mg/kg. Blood samples were analyzed for lipid and drug content by dual label liquid scintillation counting. The concentrations of vinblastine in the blood and plasma were significantly dependent on the lipid dose, particularly at later time points, as illustrated in FIGS. 8 and 9.

Example 10

Cryo-Tem Micrographs of Liposomal Vinorelbine

To better understand the mechanism of drug release and the relationship of drug release rates to D/L ratio, formulations of liposomal vinorelbine and liposomal vinblastine were examined by cryo-TEM. These micrographs revealed the presence of electron dense, amorphous precipitates inside formulations encapsulated at a D/L ratio of 0.25, w/w (FIG. 3). The presence of drug precipitates is expected to be important in regulating drug release, resulting in a slower release profile.

Example 11

Tolerability and MTD of Liposomal Vinorelbine

The tolerability and maximum tolerable dose (MTD) of free and liposomal vinorelbine were evaluated in immunodeficient (nude) and immunocompetent (ICR) mice to establish a suitable dosing range for efficacy studies.

Single and multiple (q7d×3) dose MTD studies were performed in tumor-bearing and non-tumor bearing NCr nu/nu mice, as well as healthy, outbred ICR mice. The body weights and well being of individual animals were monitored following single or multiple injections of free or liposomal vinorelbine. The MTD was defined, prior to initiation of the study, as the highest dose that would elicit a group weight loss of 20% or, if weight loss was not a good predictor of tolerability, the resulting $LD_{10}$ dose would be used. The published $LD_{50}$ for free vinorelbine is 34 mg/kg in mice.

Table 5 summarizes the weight loss and drug-related deaths associated with vinorelbine administration in nude and ICR mice. In general, 20% weight loss did not correlate well with morbidity and mortality as toxic deaths were sometimes observed at doses that resulted in less than 20% weight loss. The maximum tolerated dose of liposomal vinorelbine was estimated to be 15 mg/kg and 20 mg/kg for single dose and q7d×3 dose schedules, respectively. The MTD of free vinorelbine was estimated to be 30 mg/kg and 25-30 mg/kg for single dose and q7d×3 dose schedules, respectively. These values were used as guidelines for dosing to the MTD in the efficacy studies. In the calculation of therapeutic index (TI) in Section 5.4.3, 27.5 mg/kg and 20 mg/kg and were used as the MTD's for free and liposomal vinorelbine, respectively.

TABLE 5

Summary of Vinorelbine Tolerability and MTD-Multiple Dosing (q7d × 3)

| Drug | Dose (mg/kg) | Nudes Max % Wt Loss | DRD | ICR Max % Wt Loss | DRD | MTD |
|---|---|---|---|---|---|---|
| VRL | 30 | | 6/18 | | | ** |
| | 25 | 0/7 | | −5 | 1/15 | ** |
| | 20 | 2/37 | | −3 | 0/15 | |
| | 10 | 0/37 | | −3 | 0/15 | |
| | 5 | 0/30 | | + | 0/15 | |
| | 2.5 | 0/12 | | | | |
| Liposomal VRL | 25 | | | −11 | 6/15 | |
| | 20 | 4/37 | | −7 | 2/15 | ** |
| | 10 | 0/37 | | −2 | 0/15 | |
| | 5 | 1/37 | | + | 0/15 | |
| | 2.5 | 0/37 | | | | |

The basic toxicity profile of liposomal vinorelbine appears equivalent to the free drug and no new toxicities were evident within the scope of this study. The clinical dose-limiting toxicity of vinorelbine is myelosuppression and, more specifically, granulocytopenia. Granulocytopenia is generally reversible and not cumulative over time. The maximum reduction in granulocyte levels typically occurs at day 7-10 following treatment and repopulation is normally complete within an additional 7-14 days. Other hematological toxicities are also quite common and include leukopenia (92%), anemia (83%) and, to a much lesser extent, thrombocytopenia (5%). Peripheral neuropathy (25%) and phlebitis (7%) are also common. Granulocytopenia was significant for both free and liposomal drug. Dose-dependent reduction in other hematological parameters/cell populations were observed for both free and liposomal vinorelbine, including decreased hematocrits and platelets. Recovery of circulating blood cell populations and progenitor cells was complete in all treatment groups by at least day 28 (evaluated day 4, 14, and 28). In general, liposomal vinorelbine slowed the recovery of various hematopoietic bone marrow progenitor cells, which is consistent with similar observations for other liposomal drugs (i.e., topotecan). The MTD's of free and liposomal vinorelbine given intravenously on a q7d×3 schedule were 27.5 and 20 mg/kg/dose, respectively. Empty SM/CH liposomes were statistically equivalent to untreated animals in all parameters evaluated.

Example 12

Comparative Toxicity of Free and Liposomal Vinorelbine

A comparative (VRL vs. liposomal VRL) toxicity study was performed in healthy, outbred ICR mice. The goals of this latter study were to (1) evaluate the toxicity profiles of free and liposomal vinorelbine and to identify any new toxicities that might appear as a result of liposome encapsulation, and (2) to evaluate the relative levels and recovery of myelosuppression following the completion of treatments.

Groups of ICR mice were injected intravenously with free or liposome-encapsulated vinorelbine at 5, 10, 20 or, in some instances, 25 mg/kg/dose of vinorelbine on a q7d×3 schedule. Parameters evaluated throughout the study included animal weight loss, physical appearance and behavioral changes, blood analysis (CBC and serum chemistry panel), hematopoietic progenitor cell levels in femur bone marrow, and organ weights and gross pathology. Tissues were collected and stored for histology as required.

Maximum group weight loss was generally less than 10% of the initial body weight. Weight loss nadirs occurred 2-3 days following each injection and weights, in general, recovered fully by day 7 following injection. Despite the relatively low loss in body weight, several mice died during the study at the higher dose levels, including 6/15 and 2/15 mice at the 25 and 20 mg/kg/dose groups of liposomal vinorelbine, respectively, and 1/15 mice at 25 mg/kg free vinorelbine. Interestingly, all deaths observed in the study occurred on day 5 or 6 following either the first or second injection.

In addition to weight loss, mice in the highest dose groups for both free and liposomal vinorelbine showed ruffled coats and were generally less active than untreated animals. Several mice in the highest dose groups of both free and liposomal vinorelbine also exhibited a progressive irritation and swelling of the eye(s) and surrounding area. This appeared to be a cumulative effect, appearing first in the highest dose groups and occurring later in lower dose groups. In the clinic, severe irritation of the eye has been reported with accidental exposure to other vinca alkaloids. The eye irritation in these mice may have been caused by exposure to excreted drug in the bedding during normal grooming. In animal studies and clinical trials, ~20% of the drug is excreted in urine and 40-50% is excreted in feces. A change in the type of bedding and daily replacement of the bedding material resulted in significant improvements in the eye conditions within a few days.

Evaluation of serum chemistry parameters showed no significant changes in treated animals relative to untreated control animals. Dose-dependent decreases in various hematology parameters were observed. The most obvious changes occurred in the neutrophil population, which was almost completely abolished, in all groups of mice treated with either free or liposomal vinorelbine, at day 4 after the last injection. This is consistent with the known dose limiting toxicity, granulocytopenia. Complete recovery of circulating neutrophil levels and corresponding bone marrow progenitor cells (CFU-GM) was observed at day 14 for free vinorelbine. Partial recovery of progenitor cells was observed for liposomal vinorelbine at day 14 and complete recovery was observed by day 28. Other changes in hematological parameters included dose-dependent decreases in hematocrit and, to a lesser extent, platelet levels, consistent with anemia and thrombocytopenia as observed clinical toxicities of free vinorelbine.

In general, liposomal vinorelbine resulted in minimal-moderate delays in recovery of various hematological parameters relative to equivalent doses of the free drug. Similar results and delays in the repopulation of various blood cell populations have been observed previously for liposomal topotecan in mice. In larger animal toxicity studies, these differences and delays were much less pronounced.

On days 4, 14 and 28 following injection, groups of treated animals were necropsied and various tissues were collected, examined and weighed. Decreased spleen weights were observed in the highest dose group for both free and liposomal vinorelbine at the earliest time point. No other significant changes in tissue weights were observed at any of the time points examined. Further, no obvious abnormal pathology was noted in any of the tissues examined in any of the dosing groups.

Example 13

Efficacy of Single Doses of Free and Liposomal Vinorelbine

Vinorelbine is used clinically in the treatment of advanced NSCLC and metastatic breast cancer. To determine whether the improvements in pharmacokinetics and drug release from ESM:CH liposomes translates into improved therapeutic activity, the anti-tumor activity of single doses of liposomal vinorelbine was evaluated in several human xenograft tumor models. These studies were designed to (1) compare the relative anti-tumor activity of liposomal vinorelbine and free drug, and (2) to identify possible selective anti-tumor activity of liposomal vinorelbine against particular types of tumors.

Tumor models investigated included RXF393 (renal), MX-1 (breast), LX-1 (small cell lung cancer), PC-3 (prostate), and HT29 (colon). These models were known to be sensitive to vinorelbine. Tumor fragments were implanted subcutaneously in the flank of NCr nu/nu mice. Treatments in all tumor models were initiated as a single i.v. bolus injections of free or liposomal vinorelbine once tumors had reached 100-300 mg and had clearly demonstrated growth. Animal weights and tumor size were determined twice weekly.

The comparative anti-tumor activity of free and liposomal vinorelbine is shown in FIGS. 10-14 and summarized in Table 6.

Figure 10:
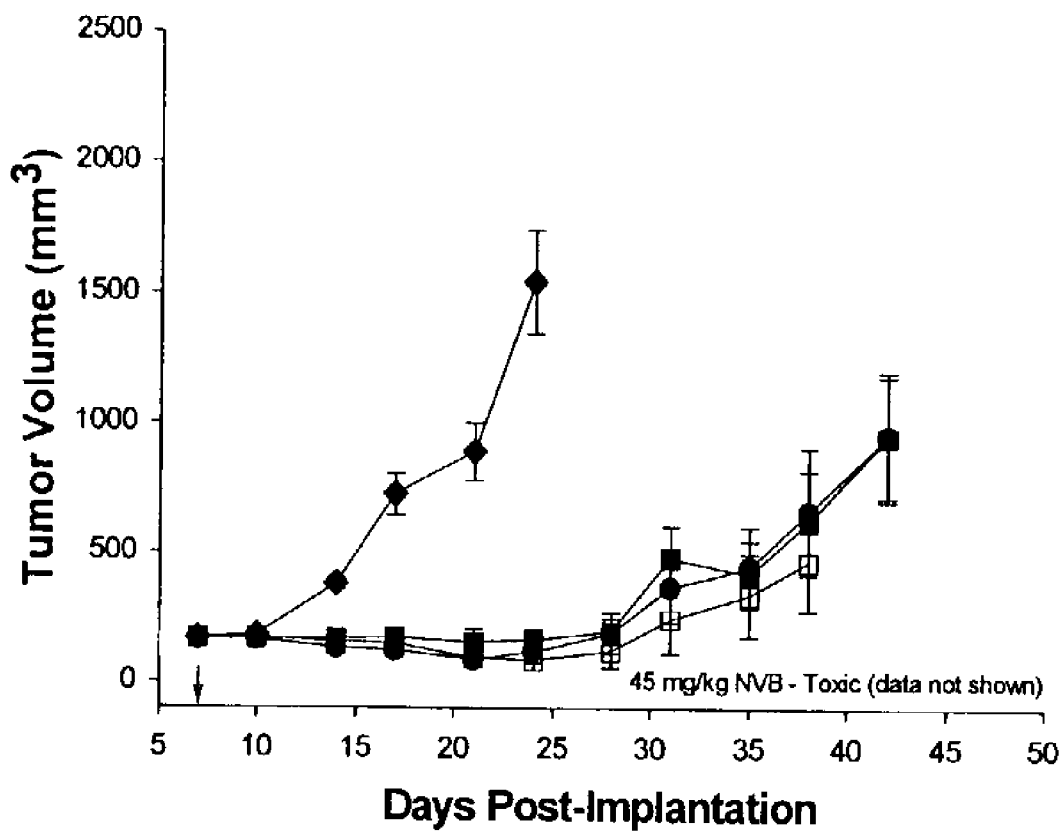
FIG. 10 shows the anti-tumor activity of single doses of free and liposomal vinorelbine in RXF393 renal xenografts. Male NCr nude mice were injected intravenously via the lateral tail vein on day 7 post-tumor-implantation with saline (♦), NVB at 45.0 mg/kg (○) and 34.0 mg/kg (□), or NVB-TCS at 15.0 mg/kg (●) and 11.0 mg/kg (■) at a drug-to-lipid ratio of 0.3:1 (w/w). The arrow on the x-axis denotes the day of drug administration. Data points represent mean±SEM (n=10).
Figure 11:
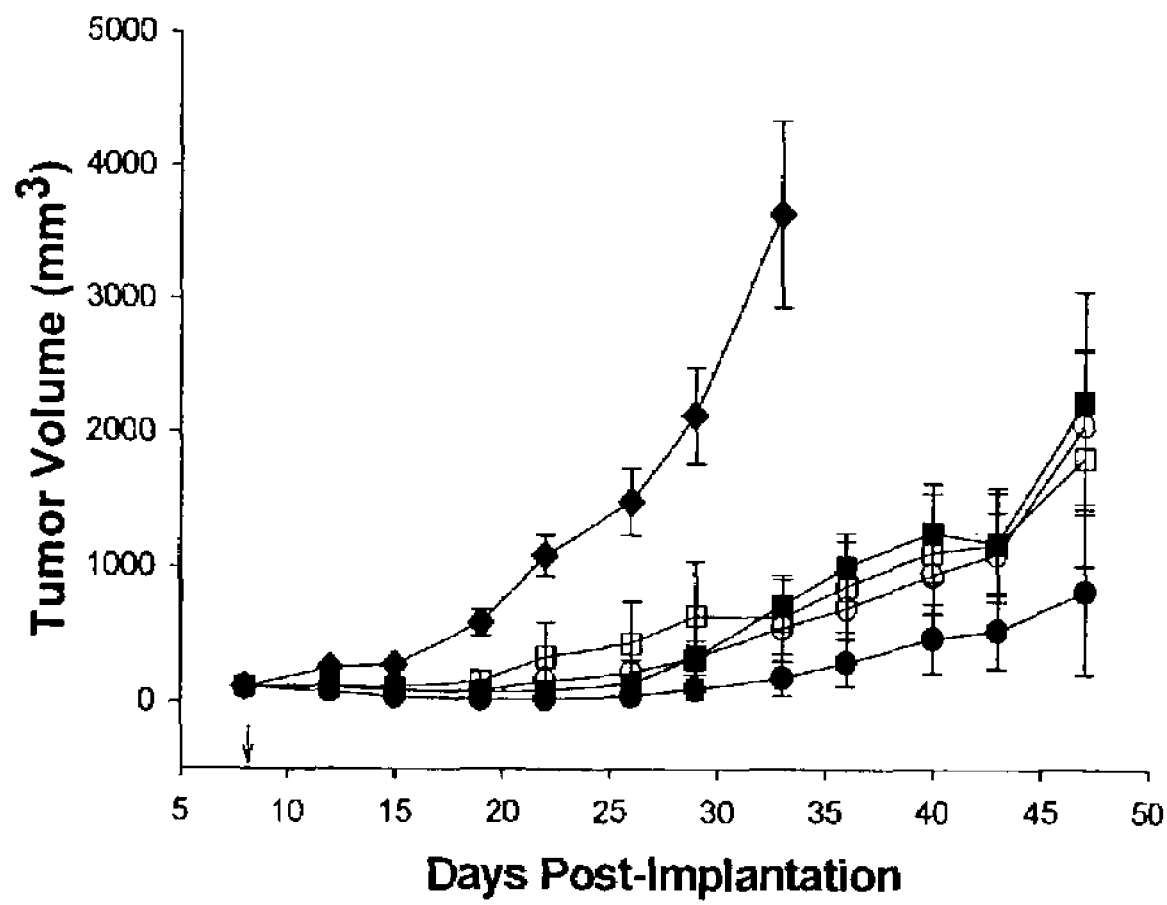
FIG. 11 shows the anti-tumor activity of single doses of free and liposomal vinorelbine in MX-1 breast xenografts. Female NCr nude mice were injected intravenously via the lateral tail vein on day 8 post-tumor-implantation with saline (♦), NVB at 34.0 mg/kg (○) and 25.5 mg/kg (□), or NVB-TCS at 15.0 mg/kg (●) and 11.0 mg/kg (■) at a drug-to-lipid ratio of 0.3:1 (w/w). The arrow on the x-axis denotes the day of drug administration. Data points represent mean±SEM (n=10).
Figure 12:
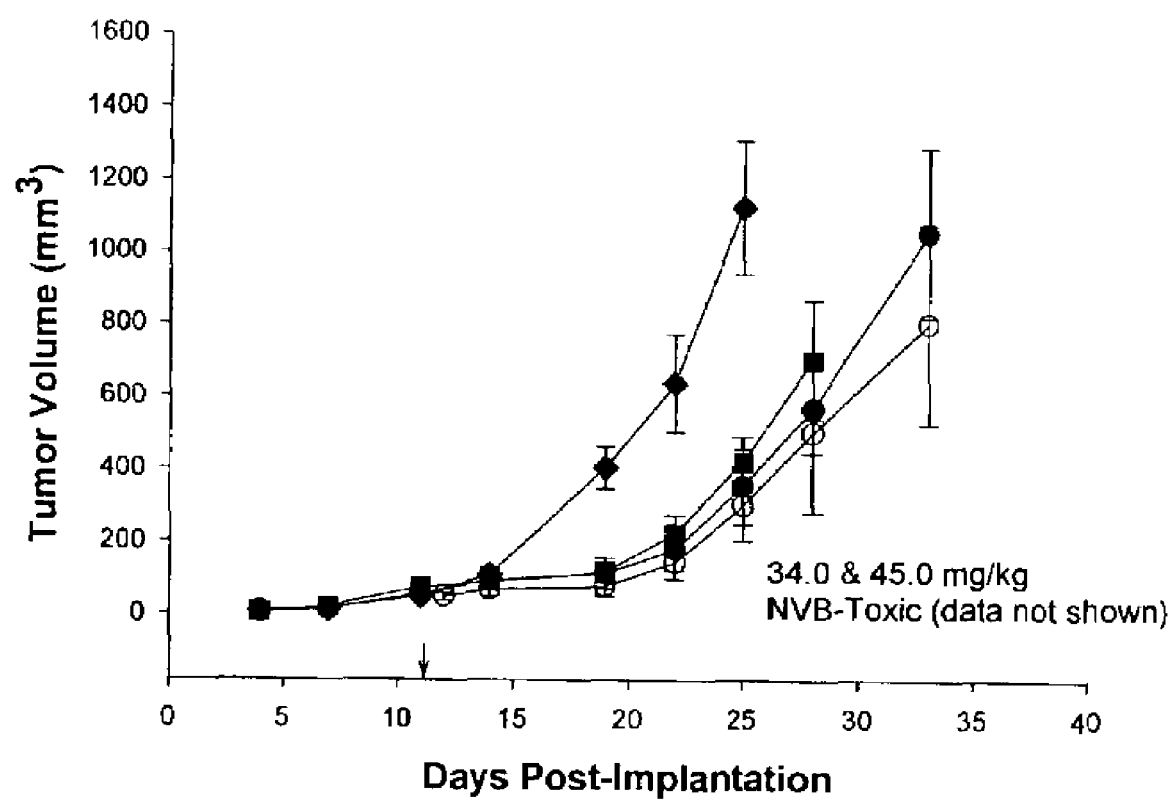
FIG. 12 shows the anti-tumor activity of single doses of free and liposomal vinorelbine in LX-1 small cell lung xenografts. Female NCr nude mice were injected intravenously via the lateral tail vein on day 11 post-tumor-implantation with saline (♦), NVB at 25.5 mg/kg (○), or NVB-TCS at 15.0 mg/kg (●) and 11.0 mg/kg (■) at a drug-to-lipid ratio of 0.3:1 (w/w). The arrow on the x-axis denotes the day of drug administration. Data points represent mean±SEM (n=7).
Figure 13:
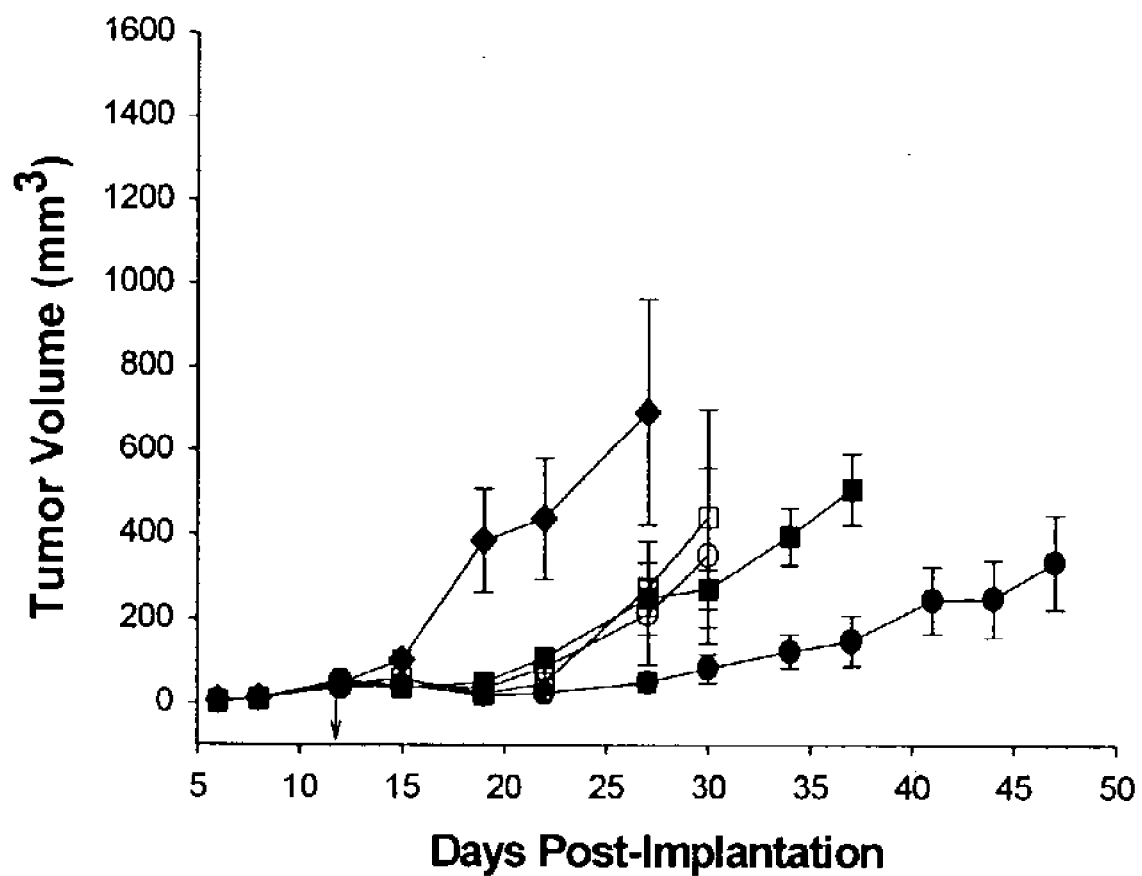
FIG. 13 shows the anti-tumor activity of single doses of free and liposomal vinorelbine in HT29 colon xenografts. Female NCr nude mice were injected intravenously via the lateral tail vein on day 12 post-tumor-implantation with saline (♦), NVB at 30.0 mg/kg (○) and 25.5 mg/kg (□), or NVB-TCS at 15.0 mg/kg (●) and 11.0 mg/kg (■) at a drug-to-lipid ratio of 0.3:1 (w/w). The arrow on the x-axis denotes the day of drug administration. Data points represent mean±SEM (n=7).
Figure 14:
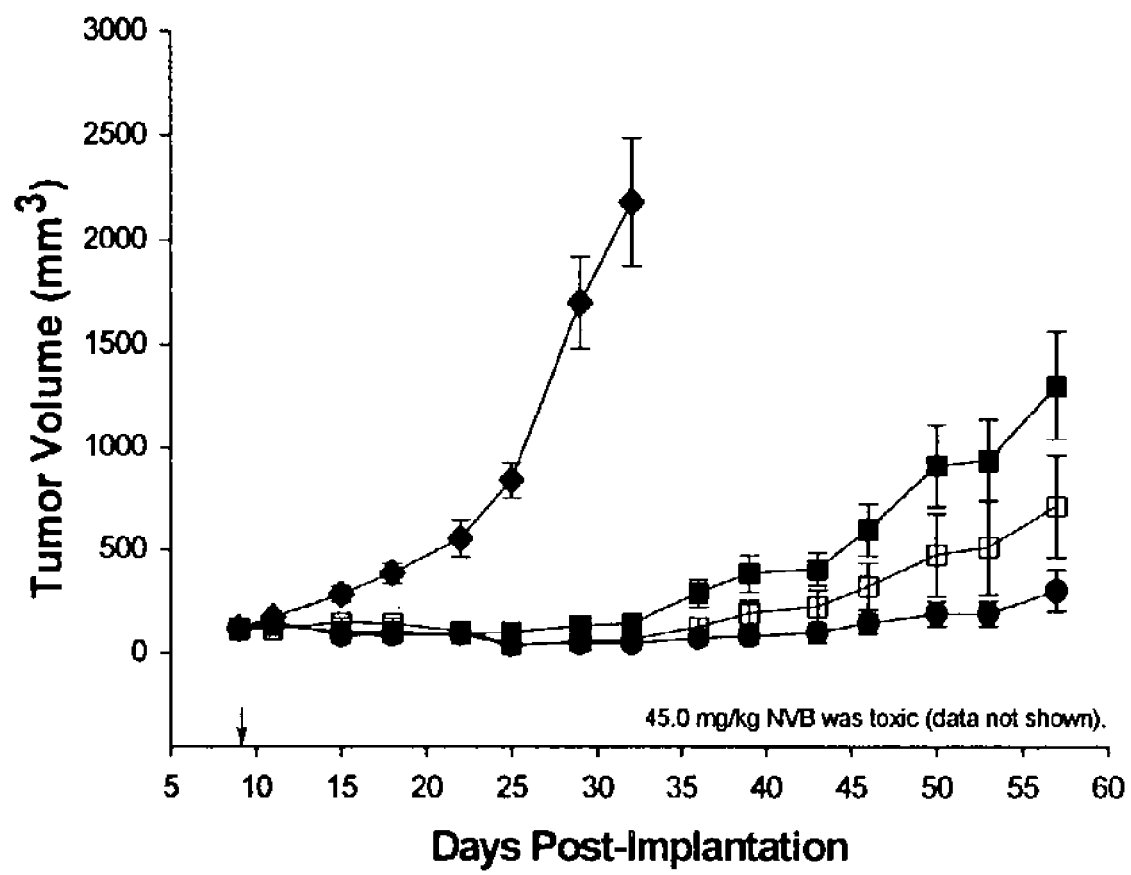
FIG. 14 shows the anti-tumor activity of single doses of free and liposomal vinorelbine in PC3 prostate xenografs. Male NCr nude mice were injected intravenously via the lateral tail vein on day 9 post-tumor-implantation with saline (♦), NVB at 45.0 mg/kg (○) and 34.0 mg/kg (□), or NVB-TCS at 15.0 mg/kg (●) and 11.0 mg/kg (■) at a drug-to-lipid ratio of 0.3:1 (w/w). The arrow on the x-axis denotes the day of drug administration. Data points represent mean±SEM (n=10).

The single dose efficacy studies in the six human xenograft tumor models demonstrated that free vinorelbine produced significant tumor growth delay in PC3 prostate, RXF 393 renal, MX-1 breast, HT-29 colon and LX-1 small cell lung models. Furthermore, the studies demonstrated that liposomal vinorelbine was as active or more active than equivalent doses of free vinorelbine in all models. Liposome encapsulation showed improved activity over the free drug in PC-3 (prostate), HT-29 (colon) and MX-1 (breast) models (FIGS. 14, 13, and 11). Both free and liposomal vinorelbine were active in RXF 393 (renal) and LX-1 (SCLC) tumor models, although no significant difference in activity was observed between free and liposomal vinorelbine (FIGS. 10 and 12).

Example 14

Efficacy of Multiple Doses of Free and Liposomal Vinorelbine

The anti-tumor activity of multiple (q7d3) dose schedules of liposomal vinorelbine was evaluated in several human xenograft tumor models. The goal of this series of studies was to identify the benefits of encapsulation by evaluating a series of doses and determining the therapeutic index in several xenograft models. Models were selected based on the following criteria: (1) activity in the single dose studies, (2) a comprehensive literature review of vinca alkaloid efficacy, (3) a desire to include at least 2-3 models that represent the clinical use of vinorelbine, and (4) a desire to include models with a range of sensitivity to vinorelbine so that improvements resulting from the use of the liposome formulation might be identified. Based on these criteria,

TABLE 6

Summary of Anti-tumor and Toxicity Parameters for Liposomal Vinorelbine in Several Human Xenograft Models

| Model | Treatment | Drug Dose (mg/kg) | Anti-Tumor Activity | | | NCI Score | Toxicity | |
|---|---|---|---|---|---|---|---|---|
| | | | % T/C[a] | T-C[b] | TF[e] | | DRD[f] | MWL[g] |
| MX-1 | VRL | 34 | 11 | 16 | 3/10 | 1 | 0/10 | −17.4 |
| (Breast) | VRL | 25.5 | 13 | 13 | 1/9 | 1 | 1/10 | −14.8 |
| | Lipo-VRL | 15 | 0 | 22 | 4/10 | 1 | 0/10 | −5.5 |
| | Lipo-VRL | 11 | 16 | 15 | 2/10 | 1 | 0/10 | −6.1 |
| LX-1 | VRL | 45 | Toxic | | | | 7/7 | |
| (SCLC) | VRL | 34 | Toxic | | | | 7/7 | |
| | VRL | 25.5 | 23 | 7 | 0/6 | 1 | 0/6 | |
| | Lipo-VRL | 15 | 34 | 6 | 0/5 | 1 | 2/7 | −16.4 |
| | Lipo-VRL | 11 | 28 | 5 | 1/7 | 1 | 0/7 | −4.7 |
| HT-29 | VRL | 30 | 31 | 9 | 1/7 | 1 | 0/7 | −9.3 |
| (Colon) | VRL | 25.5 | 35 | 12 | 1/7 | 1 | 0/7 | −9.8 |
| | Lipo-VRL | 15 | 9 | 21 | 0/7 | 1 | 0/7 | −2.3 |
| | Lipo-VRL | 11 | 41 | 6 | 0/7 | 0 | 0/7 | −3.8 |
| PC-3 | VRL | 45 | Toxic | | 4/5 | | 5/10 | −25.4 |
| (Prostate) | VRL | 34 | −3 | 34 | 1/8 | 2 | 2/10 | −18.7 |
| | Lipo-VRL | 15 | −4 | 52 | 1/6 | 2 | 4/10 | −10.0 |
| | Lipo-VRL | 11 | 1 | 27 | 0/10 | 1 | 0/10 | −3.8 |
| RXF-393 | VRL | 45 | Toxic | | 0/1 | | 9/10 | −24.6 |
| (Renal) | VRL | 34 | −6 | 22 | 2/8 | 2 | 2/10 | −23.1 |
| | Lipo-VRL | 15 | −3 | 22 | 1/7 | 2 | 3/10 | −15.7 |
| | Lipo-VRL | 11 | 0 | 11 | 1/10 | 1 | 0/10 | −3.8 |

[a]optimal % T/C following final treatment. Negative value indicates tumor regression.
[b]tumor growth delay (difference in time for treated and control tumors to reach 1000 mm$^3$).
[e]tumor free animals at the end of study (i.e. no visible tumors or long term survivors).
[f]drug related deaths.
[g]maximum mean weight loss per treatment group.
***"cures"; no visible tumors by day 60.

MX-1 and MDA-MB-435 breast models, the NCI-H460 NSCLC model and the HT-29 and DLD-1 colon models were chosen.

The comparative anti-tumor activity of free and liposomal vinorelbine is shown in FIGS. 15-19 and summarized in Table 7.

study. In the MX-1 model, encapsulation reduced the amount of drug required to exhibit equivalent activity to the free drug by 2-4 fold. The MDA-MB-435 model was very sensitive to vinorelbine, both free and encapsulated, and no significant differences in activity between the free and liposomal drug. In the MDA-MB-435 model, liposomal

TABLE 7

Summary of Multiple (q7dx3) Dose Anti-tumor and Toxicity Parameters for Liposomal Vinorelbine in Several Human Xenograft Models

| Model | Treatment | Drug Dose (mg/kg) | Anti-Tumor Activity | | | NCI Score | Toxicity | |
|---|---|---|---|---|---|---|---|---|
| | | | % T/C[a] | T-C[b] | TF[e] | | DRD[f] | MWL[g] |
| MX-1 (Breast) | VRL | 20 | −28 | 28.5 | 0 | 3 | 0 | +[h] |
| | VRL | 10 | 38 | 7.3 | 0 | 1 | 0 | |
| | VRL | 5 | 100 | 0 | 0 | 0 | 0 | |
| | VRL | 2.5 | 100 | 0 | 0 | 0 | 0 | |
| | Lipo-VRL | 20 | −100 | >60 | 0 | 4 | 0 | |
| | Lipo-VRL | 10 | −81 | 32.4 | 1 | 3 | 0 | |
| | Lipo-VRL | 5 | 29 | 24.7 | 0 | 1 | 0 | |
| | Lipo-VRL | 2.5 | 74 | 0 | 0 | 0 | 0 | |
| MDA-MB-435 (Breast) | VRL | 30 | −100 | >62 | 3 | 4 | 1 | |
| | VRL | 20 | −100 | >62 | 4 | 4 | 2 | |
| | VRL | 10 | −100 | >62 | 1 | 3 | 0 | |
| | VRL | 5 | −3 | 37.5 | 0 | 2 | 0 | |
| | Lipo-VRL | 20 | −100 | >62 | 1 | 4 | 3 | |
| | Lipo-VRL | 10 | −100 | 59.7 | 0 | 3 | 0 | |
| | Lipo-VRL | 5 | 3 | 32.9 | 0 | 1 | 0 | |
| | Lipo-VRL | 2.5 | 31 | 15.8 | 0 | 0 | 0 | |
| | Paclitaxel | 15 | −55 | 36.9 | 0 | 3 | | |
| NCI-H460 (NSCLC) | VRL | 30 | 10 | 19.1 | 0 | 1 | 2 | |
| | VRL | 20 | 30 | 9.1 | 0 | 1 | 0 | |
| | VRL | 10 | 45 | 6.2 | 0 | 0 | 0 | |
| | VRL | 5 | 63 | 2.8 | 0 | 0 | 0 | |
| | Lipo-VRL | 20 | −6 | 26.9 | 1 | 2 | 0 | |
| | Lipo-VRL | 10 | 11 | 16.2 | 0 | 1 | 0 | |
| | Lipo-VRL | 5 | 57 | 5 | 0 | 0 | 0 | |
| | Lipo-VRL | 2.5 | 75 | 4 | 0 | 0 | 0 | |
| | Mitomycin C | 3 | 5 | 22.2 | 0 | 1 | 0 | |
| HT-29 (Colon) | VRL | 20 | −65 | 29.3 | 1 | 3 | 0 | |
| | VRL | 10 | 5 | 11.9 | 0 | 1 | 0 | |
| | VRL | 5 | 67 | 1.32 | 0 | 0 | 0 | |
| | VRL | 2.5 | 104 | 0 | 0 | 0 | 0 | |
| | Lipo-VRL | 20 | −100 | >85 | 3 | 4 | 0 | |
| | Lipo-VRL | 10 | −94 | >85 | 3 | 3 | 0 | |
| | Lipo-VRL | 5 | −2 | 24.2 | 1 | 2 | 0 | |
| DLD-1 (Colon) | VRL | 30 | −100 | 26.4 | 0 | 3 | 2 | |
| | VRL | 20 | −36 | 19.7 | 0 | 2 | 0 | |
| | VRL | 10 | 58 | 4.7 | 0 | 0 | 0 | |
| | VRL | 5 | 88 | 0.0 | 0 | 0 | 0 | |
| | Lipo-VRL | 20 | −100 | 36.5 | 1 | 3 | 1 | |
| | Lipo-VRL | 10 | −35 | 32.1 | 0 | 2 | 0 | |
| | Lipo-VRL | 5 | 66 | 3.0 | 0 | 0 | 1 | |
| | Lipo-VRL | 2.5 | 93 | 0.0 | 0 | 0 | 0 | |
| | Irinotecan | 90 | 11 | 17.2 | 0 | 1 | 0 | |

[a]optimal % T/C following final treatment. Negative value indicates tumor regression.
[b]tumor growth delay (difference in time for treated and control tumors to reach 1000 mm³).
[e]tumor free animals at the end of study (i.e. no visible tumors or long term survivors).
[f]drug related deaths (n = 6).
[g]maximum mean weight loss per treatment group.
**"cures"; no visible tumors by day 60.

Figure 15:
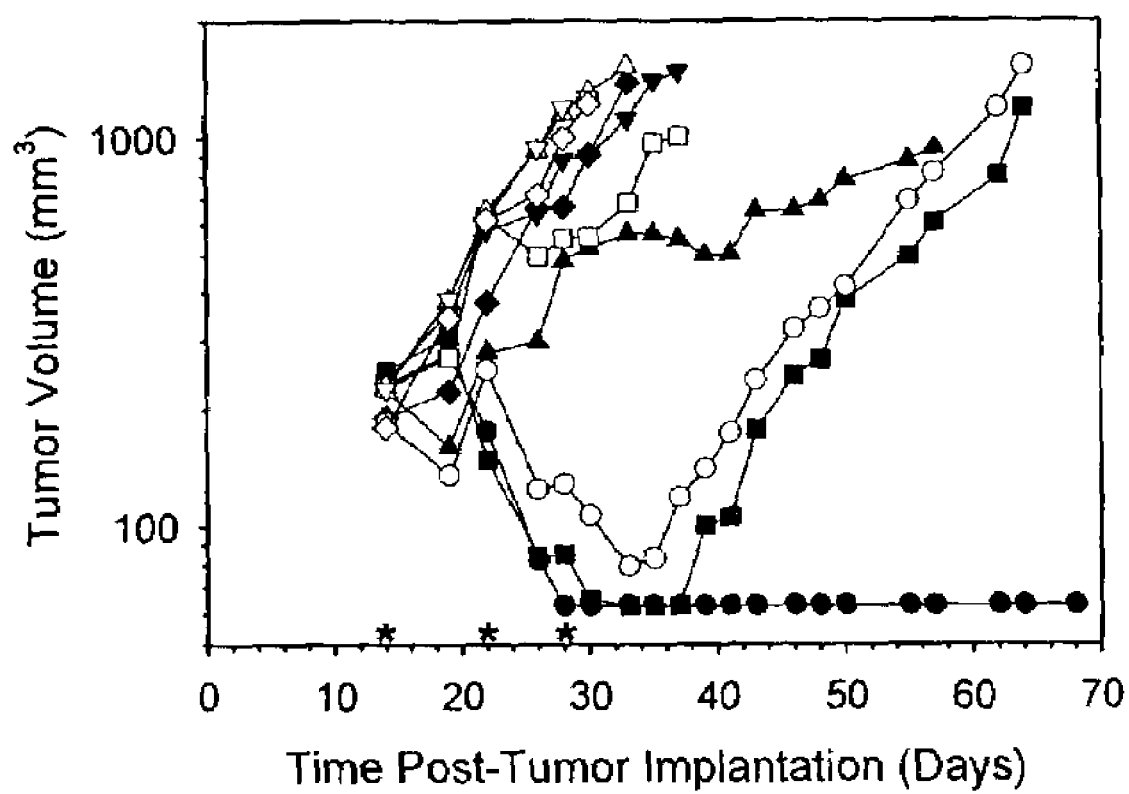
FIG. 15 shows the anti-tumor activity of multiple doses of free and liposomal vinorelbine in MX-1 breast xenografts. Female NCr nude mice were injected intravenously (q7d×3) via the lateral tail vein on days indicated by an asterisk (*). Symbols represent: saline (♦); free VRL, 20 mg/kg/dose (♦); free VRL, 10 mg/kg/dose (□); free VRL, 5 mg/kg/dose (Δ); free VRL, 2.5 mg/kg/dose (∇); liposomal VRL, 20 mg/kg/dose ('); liposomal VRL, 10 mg/kg/dose (■);liposomal VRL, 5 mg/kg/dose (▲); liposomal VRL, 2.5 mg/kg/dose (▼) and empty liposomes (◇). Drug-to-lipid ratio was 0.3/1 (w/w). Data points represent median tumor volume (n=6).
Figure 16:
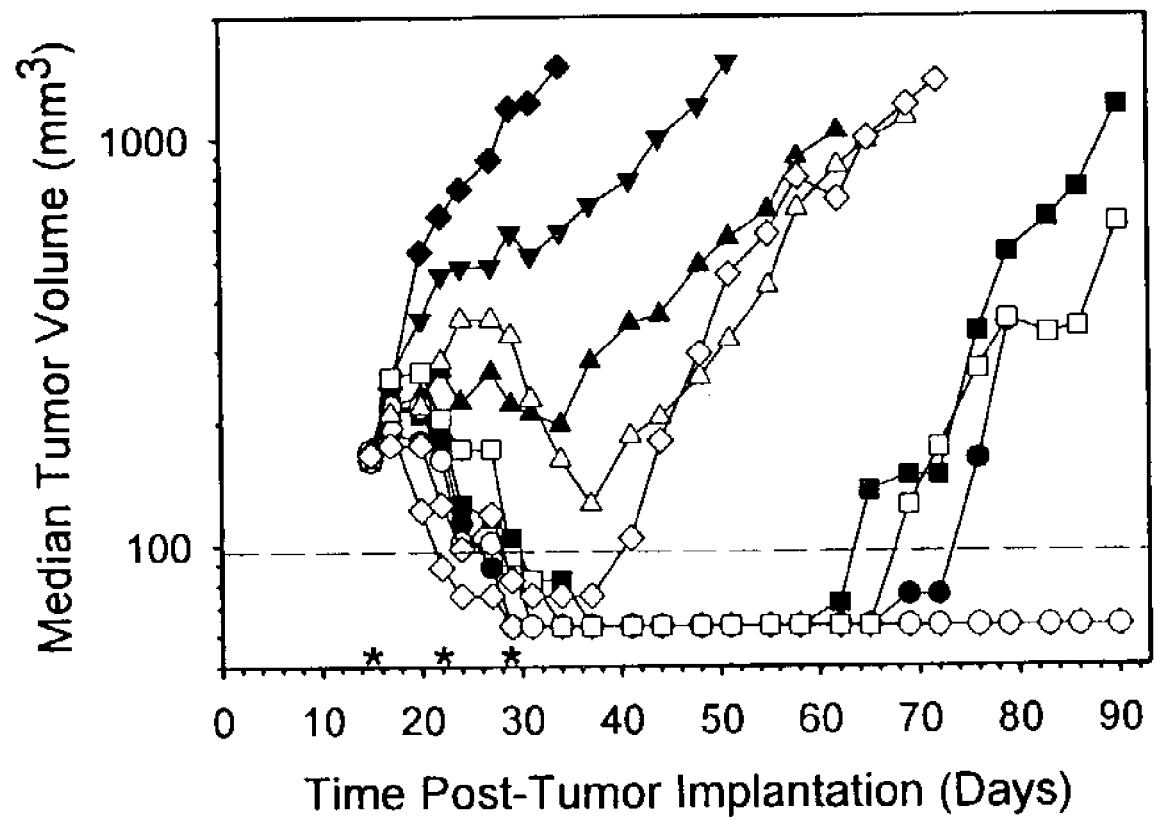
FIG. 16 shows the anti-tumor activity of multiple doses of free and liosomal vinorelbine in MDA-MB-435 breast xenografts. Female NCr nude mice were injected intravenously (q7d×3, beginning day 15) via the lateral tail vein. Symbols represent: saline (♦); free VRL, 20 mg/kg/dose (♦); free VRL, 10 mg/kg/dose (□); free VRL, 5 mg/kg/dose (Δ); free VRL, 2.5 mg/kg/dose (∇); liposomal VRL, 20 mg/kg/dose ('); liposomal VRL, 10 mg/kg/dose (■); liposomal VRL, 5 mg/kg/dose (▲); liposomal VRL, 2.5 mg/kg/dose (▼). Paclitaxel (◇) was prepared in 12/5% cremophor/12.5% ethanol/75% saline and injected iv (q1d×5) at a dose of 15 mg/kg/dose. Drug-to-lipid ratio was 0.3/1 (w/w). Data points represent median tumor volume (n=6).

Significant anti-tumor activity was observed for liposomal vinorelbine in the two breast models examined, MX-1 and MDA-MB-435 (FIGS. 15 and 16). In both models, NCI scores of 4 (highest score on a 0-4 scale) were obtained at two different dose levels (Table 23). An NCI score of 4 indicates tumor regression in some or all of the animals and at least 30% of treated mice are tumor-free at the end of the study.

vinorelbine outperformed the dose and schedule optimized (determined by Southern Research Institute) positive control for this model—paclitaxel (15 mg/kg/dose, qd×5).

Figure 17:
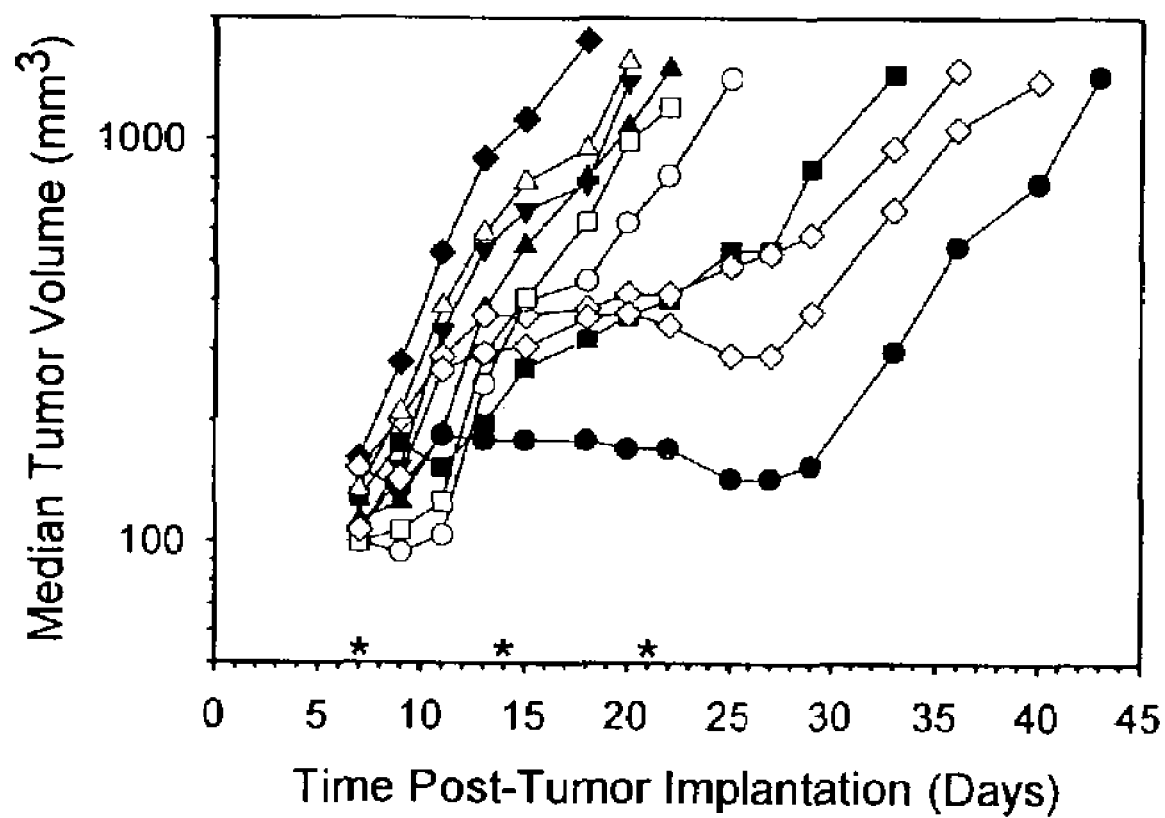
FIG. 17 shows the anti-tumor activity of multiples doses of free and liposomal vinorelbine in NCI H460 non small cell lung xenografts. Female NCr nude mice were injected intravenously (q7d×3, beginning day 7) via the lateral tail vein. Symbols represent: saline (♦); free VRL, 20 mg/kg/dose (♦); free VRL, 10 mg/kg/dose (□); free VRL, 5 mg/kg/dose (Δ); free VRL, 2.5 mg/kg/dose (∇); liposomal VRL, 20 mg/kg/dose ('); liposomal VRL, 10 mg/kg/dose (■); liposomal VRL, 5 mg/kg/dose (▲); liposomal VRL, 2.5 mg/kg/dose (▼). Mitomycin C (◇) was prepared in saline and injected iv (q4d×3) at a dose of 3 mg/kg/dose. Drug-to-lipid ratio was 0.3/1 (w/w). Data points represent median tumor volume (n=6).

In the NCI-H460 NSCLC model, the liposomal formulation of vinorelbine showed substantial tumor growth inhibition and produced significant improvements in several of the efficacy parameters examined, including % T/C and tumor growth delay (FIG. 17 and Table 7). NCI scores of 1 were obtained at 3 of 4 dose levels, indicating varying degrees of tumor inhibition. Overall, liposomal vinorelbine was 2-3 fold more active than equivalent doses of free drug. Interestingly, liposomal vinorelbine outperformed the dose and schedule optimized (determined by Southern Research Institute) positive control for this model—mitomycin C (3 mg/kg/dose, q4dx3).

Figure 18:
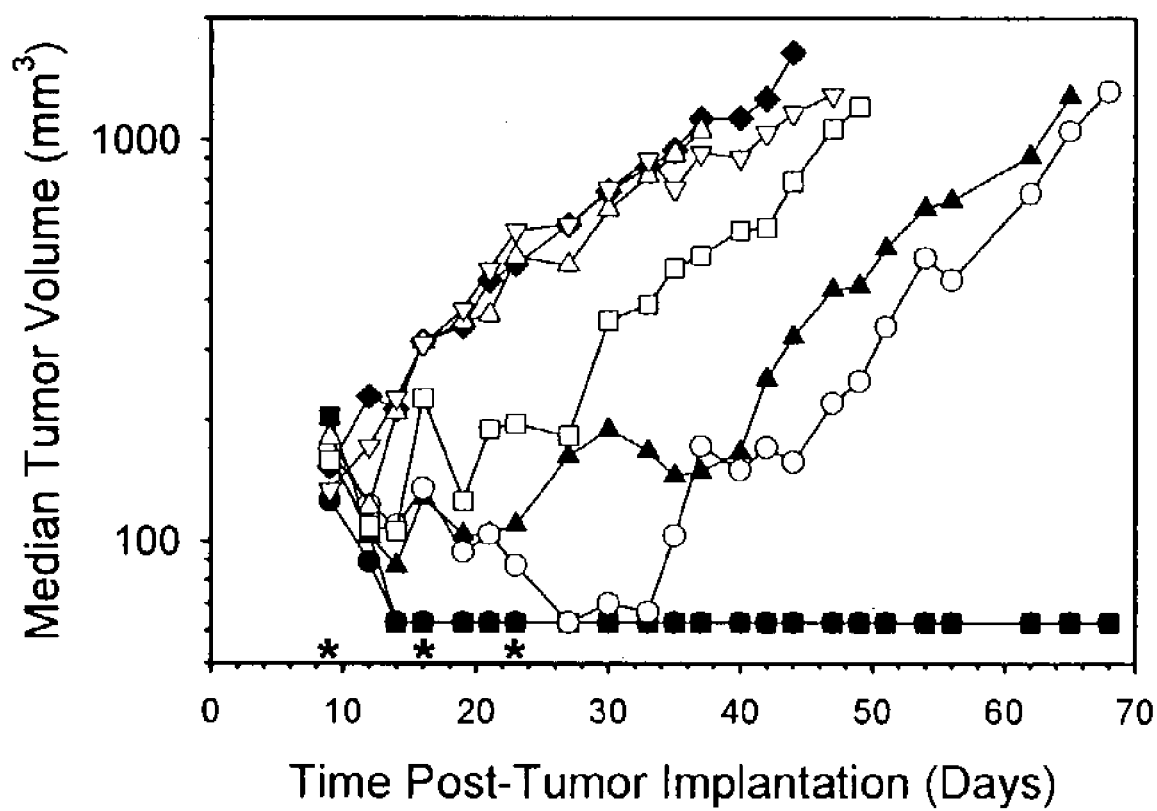
FIG. 18 shows the anti-tumor activity of multiple doses of free and liposomal vinorelbine in HT29 colon xenografts. Female NCr nude mice were injected intravenously (q7d×3) via the lateral tail vein on days indicated by an asterisk (*). Symbols represent: saline (♦); free VRL, 20 mg/kg/dose (♦); free VRL, 10 mg/kg/dose (□); free VRL, 5 mg/kg/dose (Δ); free VRL, 2.5 mg/kg/dose (∇); liposomal VRL, 20 mg/kg/dose ('); liposomal VRL, 10 mg/kg/dose (■); liposomal VRL, 5 mg/kg/dose (▲). Drug-to-lipid ratio was 0.3/1 (w/w). Data points represent median tumor volume (n=6).
Figure 19:
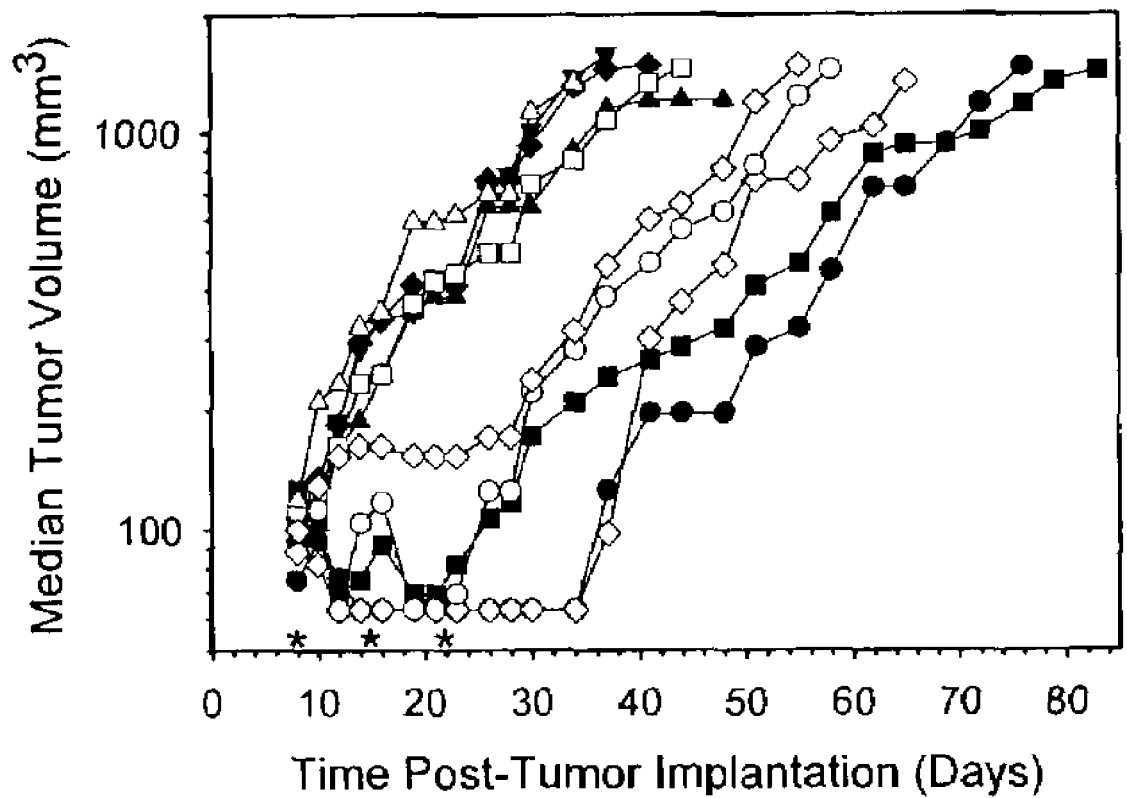
FIG. 19 shows the anti-tumor activity of multiple doses of free and liposomal vinorelbine in DLD-1 colon xenografts. Female NCr nude mice were injected intravenously (q7d×3) via the lateral tail vein on days indicated by an asterisk (*). Symbols represent: saline (♦); free VRL, 20 mg/kg/dose (♦); free VRL, 10 mg/kg/dose (□); free VRL, 5 mg/kg/dose (Δ); free VRL, 2.5 mg/kg/dose (∇); liposomal VRL, 20 mg/kg/dose ('); liposomal VRL, 10 mg/kg/dose (■); liposomal VRL, 5 mg/kg/dose (▲); liposomal VRL, 2.5 mg/kg/dose (▼). Irinotecan (◇) was prepared in saline and injected iv (q4d×3) at a dose of 90 mg/kg/dose. Drug-to-lipid ratio was 0.3/1 (w/w). Data points represent median tumor volume (n=6).

Strong anti-tumor activity was also observed in the two colon models examined, HT-29 and DLD-1 (FIGS. 18 and 19). NCI activity scores of 4 were obtained for the two highest dose groups in the HT-29 model and scores of 4 and 3 were obtained in the same dose groups in the DLD-1 model (Table 7). In both models, significant tumor regression and tumor free animals were observed during the course of the studies. Overall, 2-fold and 4-fold increases in anti-tumor activity were observed for HT-29 and DLD-1, respectively. Liposomal vinorelbine also outperformed the SRI positive control in the DLD-1 model—irinotecan (90 mg/kg/dose, q4dx3).

In summary, liposomal vinorelbine was very active in all 5 xenograft models examined (including 2 breast, 1 NSCLC, and 2 colon models), using a q7dx3 dosing schedule. Improvements in anti-tumor activity relative to free drug were noted in 4 of 5 models and were generally characterized by a 2-4 fold increase in activity. Liposomal vinorelbine outperformed all three of SRI's model and dose-optimized positive controls for anti-tumor activity. The therapeutic index for liposomal vinorelbine was high in all models (4.4-10), and improvements in therapeutic index relative to free drug were observed in 4 of 5 models (3.6x, 2.4x, 2.0x, 1.4x and 1.0x). These data strongly support the earlier single dose studies described in Example 13 and further demonstrate the anti-tumor activity of liposomal vinorelbine.

Example 15

Relative Therapeutic Index of Free and Liposomal Vinorelbine in Human Tumor Xenografts Therapeutic index (TI) is a parameter that quantifies the "safety factor" of a particular therapy. TI is a ratio of a toxicity parameter and a biological activity parameter. Therefore, a higher ratio represents a greater potential margin of safety. For these studies, TI is defined as follows:

$$TI = MTD/MED$$

The minimal effective dose (MED) was set according to NCI activity criteria as the dose resulting in an optimal % T/C of 40. This information was derived from Table 7. The maximum tolerable dose (MTD) values, 27.5 and 20 mg/kg for free and liposomal vinorelbine, respectively, were derived from Table 5.

TABLE 8

Relative Therapeutic Indices of Free and Liposomal Vinorelbine in Human Tumor Xenograft Models Treated Intravenously q7d × 3[a]

| Tumor Model | Vinorelbine | | |
|---|---|---|---|
| | $TI_{Free}$ | $TI_{Lipo}$ | $TI_{Lipo}/TI_{Free}$ |
| MX-1 (breast) | 4.7 | 2.4 | 2.0 |
| MDA-MB-435 (breast) | 10.0 | 9.9 | 1.0 |
| NCl-H460 (NSCLC) | 3.0 | 1.0 | 1.6 |
| HT29 (Colon) | 8.8 | 3.7 | 2.4 |
| DLD-1 (Colon) | 3.4 | 2.4 | 1.4 |

[a]TI calculated based on the formula, TI = MTD/MED, where MED is the minimal effect dose (% T/C = 40). The MTD values were derived from TABLE X—X and were 27.5 and 20 mg/kg for free and liposomal vinorelbine, respectively.

Using this information, the TI for each treatment and model was calculated and is shown in Table 8. With the exception of the MDA-MB-435 model, free vinorelbine had a TI of 2.0-2.5 in all of the models examined. Increases in therapeutic index were observed for liposomal vinorelbine in 4 of 5 models (1.4-3.6 fold increases). The MDA-MB-435 breast model was very sensitive to both free and liposomal vinorelbine. Both treatments had a TI of ~10.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a solid tumor in a mammal, comprising administering to said mammal a pharmaceutical composition comprising liposome-encapsulated vinorelbine, wherein the said solid tumor is selected from the group consisting of lung cancer, breast cancer, colon cancer, prostate cancer and renal cancer.

2. The method of claim 1, wherein the pharmaceutical composition is administered to said mammal every seven days.

3. The method of claim 2, wherein said pharmaceutical composition is administered to said mammal for at least three weeks.

4. The method of claim 2, wherein the therapeutic index of the pharmaceutical composition is greater than the therapeutic index of free vinorelbine.

5. The method of claim 4, wherein the therapeutic index of the pharmaceutical composition is at least 1.4-fold greater than the therapeutic index of free vinorelbine.

6. The method of claim 4, wherein the therapeutic index of the pharmaceutical composition is at least 2-fold greater than the therapeutic index of free vinorelbine.

7. The method of claim 4, wherein the therapeutic index of the pharmaceutical composition is at least 2.4-fold greater than the therapeutic index of free vinorelbine.

8. The method of claim 4, wherein the therapeutic index of the pharmaceutical composition is at least 3.6-fold greater than the therapeutic index of free vinorelbine.

9. The method of claim 1, wherein the liposome comprises sphingomyelin and cholesterol.

10. The method of claim 9, wherein the ratio of sphingomyelin to cholesterol is between 75/25 and 50/50 (mol % sphingomyelin/mol % cholesterol).

11. The method of claim 10, wherein the ration of sphingomyelin to cholesterol is approximately 55:45 (mol % sphingomyelin/mol % cholesterol).

12. The method of claim 1, wherein the ratio of vinorelbine to lipid is 0.001-0.5:1 (w/w).

13. The method of claim 12, wherein the ratio of vinorelbine to lipid is at least 0.1:1 (w/w).

14. The method of claim 13, wherein the ratio of vinorelbine to lipid is 0.1-0.3:1 (w/w).

* * * * *